United States Patent
Ghosh

(10) Patent No.: US 9,999,775 B2
(45) Date of Patent: Jun. 19, 2018

(54) SYSTEM AND METHOD FOR CONTROLLING CARDIAC PACING MODE SWITCHING

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days. days.

(21) Appl. No.: 15/223,703

(22) Filed: Jul. 29, 2016

(65) Prior Publication Data
US 2018/0028814 A1    Feb. 1, 2018

(51) Int. Cl.
| | |
|---|---|
| *A61N 1/36* | (2006.01) |
| *A61N 1/368* | (2006.01) |
| *A61N 1/365* | (2006.01) |
| *A61N 1/372* | (2006.01) |
| *A61N 1/375* | (2006.01) |
| *A61N 1/39* | (2006.01) |

(52) U.S. Cl.
CPC ....... *A61N 1/3688* (2013.01); *A61N 1/36578* (2013.01); *A61N 1/3756* (2013.01); *A61N 1/37205* (2013.01); *A61N 1/37288* (2013.01); *A61N 1/3962* (2013.01)

(58) Field of Classification Search
CPC .............. A61N 1/3688; A61N 1/36578; A61N 1/3962; A61N 1/3714
See application file for complete search history.

(56) References Cited

U.S. PATENT DOCUMENTS

| | | |
|---|---|---|
| 4,624,260 A | 11/1986 | Baker, Jr. et al. |
| 4,987,897 A | 1/1991 | Funke |
| 5,144,949 A | 9/1992 | Olson |
| 5,507,782 A | 4/1996 | Kieval et al. |
| 5,893,882 A | 4/1999 | Peterson et al. |
| 6,434,424 B1 | 8/2002 | Igel et al. |
| 6,889,083 B2 | 5/2005 | Kleckner et al. |
| 7,142,918 B2 | 11/2006 | Stahmann et al. |
| 7,761,150 B2 | 7/2010 | Ghanem et al. |
| 8,433,409 B2 | 4/2013 | Johnson et al. |
| 8,457,739 B2 | 6/2013 | Kornet et al. |
| 8,532,785 B1 | 9/2013 | Crutchfield et al. |
| 8,541,131 B2 | 9/2013 | Lund et al. |
| 2012/0172892 A1 | 7/2012 | Grubac et al. |
| 2013/0282073 A1 | 10/2013 | Cowan et al. |
| 2015/0306375 A1 | 10/2015 | Marshall et al. |
| 2015/0306410 A1 | 10/2015 | Marshall et al. |
| 2015/0321011 A1 | 11/2015 | Carney et al. |

(Continued)

OTHER PUBLICATIONS

Ghosh et al., "Atrial Tracking in an Intracardiac Ventricular Pacemaker", U.S. Appl. No. 15/140,585, filed Apr. 28, 2016, 50 pages.

(Continued)

*Primary Examiner* — Paula J Stice

(57) ABSTRACT

An implantable medical device system operates in an atrial synchronized ventricular pacing mode and switches to an atrial-asynchronous pacing mode when pacing mode switching criteria are met. A control circuit of the system detects a cycle length change between two atrial cycle lengths determined from a cardiac signal that includes far-field atrial events. If the cycle length change is greater than a change, threshold the control circuit determines if the pacing mode switching criteria are satisfied subsequent to detecting the cycle length change.

27 Claims, 11 Drawing Sheets

(56) References Cited

U.S. PATENT DOCUMENTS

| | | |
|---|---|---|
| 2015/0321012 A1 | 11/2015 | Cinbis et al. |
| 2015/0321016 A1 | 11/2015 | O'Brien et al. |
| 2016/0114169 A1 | 4/2016 | Sheldon et al. |
| 2016/0144190 A1 | 5/2016 | Cao et al. |
| 2016/0158567 A1 | 6/2016 | Marshall et al. |

OTHER PUBLICATIONS

Thompson-Nauman et al., "Extra-Cardiovascular Cardiac Pacing System" U.S. Appl. No. 14/957,651, filed Dec. 3, 2015, 65 pages.

Anderson et al., "Extra-Cardiovascular Pacing Using High-Voltage Therapy Circutry of an Implantable Cardioverter Defibrillator", U.S. Appl. No. 62/262,499, filed Dec. 3, 2015, 72 pages.

Anderson et al., "Extra-Cardiovascular Cardiac Pacing System for Delivering Composite Pacing Pulses", U.S. Appl. No. 62/262,412, filed Dec. 3, 2015, 70 pages.

SYSTEM AND METHOD FOR CONTROLLING CARDIAC PACING MODE SWITCHING

TECHNICAL FIELD

The disclosure relates generally to implantable medical device systems and methods for switching between atrial-synchronized and atrial-asynchronous ventricular pacing modes.

BACKGROUND

Implantable medical devices (IMDs), such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart.

Single chamber pacemakers sense cardiac electrical signals in a single heart chamber and deliver pacing pulses to the heart chamber in the absence of electrical activity. Dual chamber pacemakers sense cardiac electrical signals in two heart chambers, e.g., in the atrial and ventricular chambers, and may deliver cardiac pacing pulses in one or both chambers to provide appropriate timing and synchrony between the contractions of the atrial and ventricular chambers.

SUMMARY

In general, the disclosure is directed to techniques for controlling automatic switching between an atrial-synchronized ventricular pacing mode and an atrial-asynchronous ventricular pacing mode based on a cardiac signal including far-field atrial events. An IMD system operating according to the techniques disclosed herein may determine atrial cycle lengths or other atrial time intervals based on atrial events sensed from the cardiac signal. The IMD system determines whether pacing mode switching criteria are met based on an analysis of the atrial cycle length and/or other atrial time intervals and operates to deliver ventricular pacing to a patient's heart according to the selected pacing mode.

In one example, the disclosure provides an implantable medical device system including a sensing circuit configured to receive a cardiac signal comprising far-field atrial events; a therapy delivery circuit configured to deliver ventricular pacing pulses via electrodes coupled to the therapy delivery circuit; and a control circuit configured to control the therapy delivery circuit to deliver the ventricular pacing pulses in an atrial-synchronized pacing mode. During the atrial synchronized pacing mode, the control circuit determines atrial cycle lengths between far-field atrial events sensed from the cardiac signal, detects a cycle length change between two atrial cycle lengths that is greater than a cycle length change threshold, determines if pacing mode switching criteria are satisfied subsequent to detecting the cycle length change, and in response to the pacing mode switching criteria being satisfied, switches from the atrial-synchronized ventricular pacing mode to an atrial-asynchronous pacing mode for controlling the therapy delivery circuit in delivering the ventricular pacing pulses.

In another example, the disclosure provides a method for controlling a ventricular pacing mode by an IMD system. The method includes receiving a cardiac signal comprising far-field atrial events; controlling a therapy delivery circuit to deliver ventricular pacing pulses in an atrial-synchronized pacing mode; during the atrial synchronized pacing mode, determining atrial cycle lengths between far-field atrial events sensed from the cardiac signal; detecting a cycle length change between two atrial cycle lengths that is greater than a cycle length change threshold; determining if pacing mode switching criteria are satisfied subsequent to detecting the cycle length change; and in response to the pacing mode switching criteria being satisfied, switching from the atrial-synchronized ventricular pacing mode to an atrial-asynchronous pacing mode for controlling the therapy delivery circuit in delivering the ventricular pacing pulses.

In another example, the disclosure provides a non-transitory, computer-readable storage medium comprising a set of instructions which, when executed by a control circuit of an IMD system, cause the system to receive a cardiac signal comprising far-field atrial events; deliver ventricular pacing pulses in an atrial-synchronized pacing mode; during the atrial synchronized pacing mode, determine atrial cycle lengths between far-field atrial events sensed from the cardiac signal; detect a cycle length change between two atrial cycle lengths that is greater than a cycle length change threshold; determine if pacing mode switching criteria are satisfied subsequent to detecting the cycle length change; and in response to the pacing mode switching criteria being satisfied, switch from the atrial-synchronized ventricular pacing mode to an atrial-asynchronous pacing mode for controlling delivery of the ventricular pacing pulses.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for controlling mode switching between atrial-synchronized ventricular pacing and asynchronous ventricular pacing in an implantable medical device (IMD) system. During atrial-synchronized ventricular pacing, ventricular pacing pulses are triggered when an atrial event is sensed so that ventricular pacing pulses track atrial events, e.g., by delivering ventricular pacing pulses at a programmed atrioventricular (AV) delay interval. Ventricular pacing pulses are inhibited when a ventricular intrinsic event, e.g., an R-wave, is sensed prior to a scheduled pacing pulse, e.g., during the AV delay interval. This pacing mode is sometimes referred to as a VDD or VDDR pacing mode, indicating single-chamber ventricular pacing, dual chamber sensing, and a dual response to sensed events that includes triggering and inhibiting the ventricular pacing pulses as indicated above (the R designating a rate response mode to meet patient activity and metabolic demand). During atrial-asynchronous ventricular pacing, ventricular pacing pulses do not track atrial events. Ventricular pacing pulses are delivered at a programmed V-V interval, sometimes referred to as ventricular pacing escape interval, and are inhibited if an intrinsic ventricular event is sensed during the pacing escape interval. This pacing mode may be referred to as a VDI or VDIR pacing mode, indicating single-chamber ventricular pacing, dual chamber sensing, and a response of inhibiting a scheduled pacing pulse when an intrinsic event is sensed.

Figure 1A:
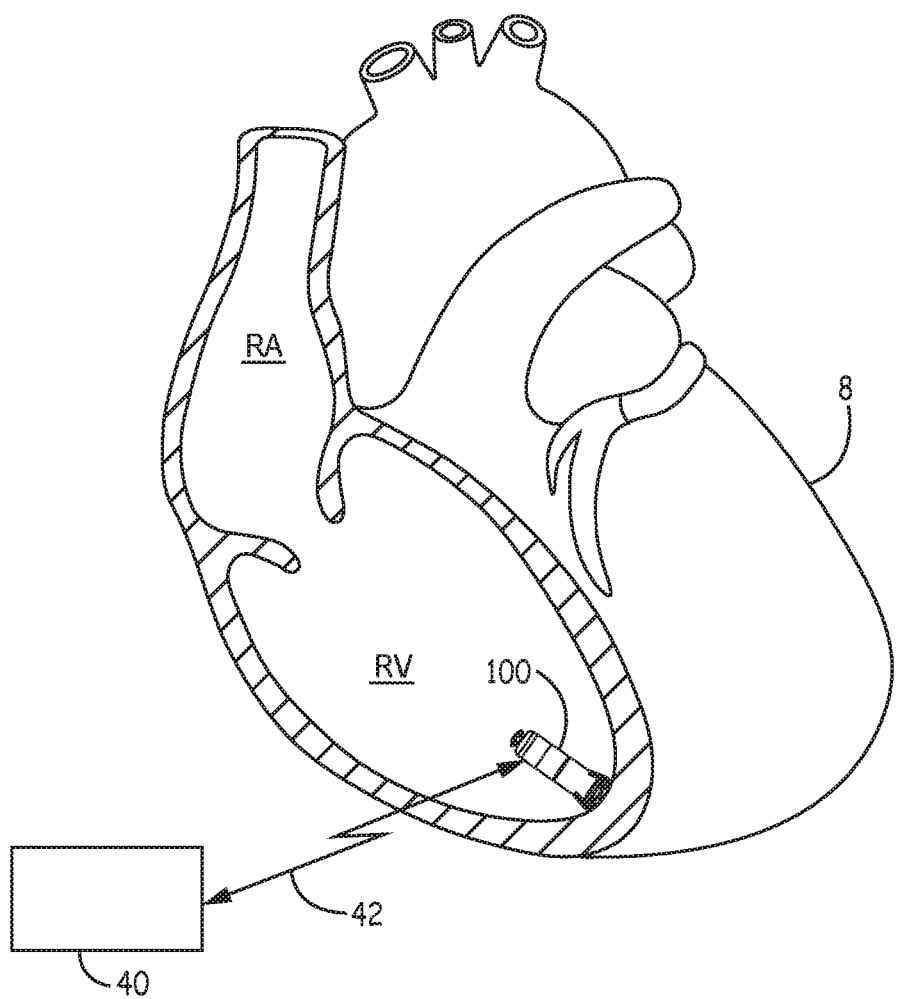
FIG. 1A is a conceptual diagram of one IMD system in which the methods disclosed herein for controlling ventricular pacing mode switching may be implemented.
Figure 1B:
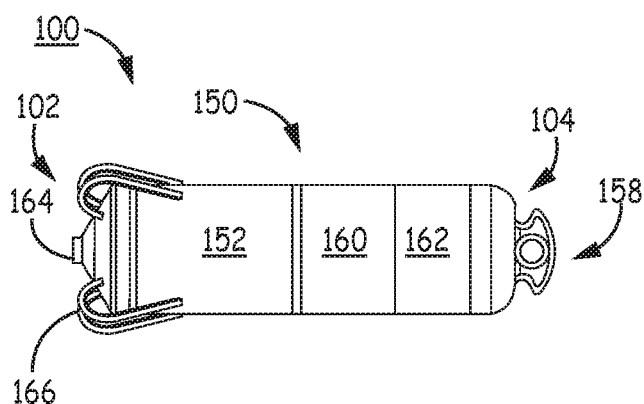
FIG. 1B is a diagram of the intra-cardiac pacemaker of FIG. 1A.

FIG. 1A is a conceptual diagram of one IMD system in which the methods disclosed herein for controlling pacing mode switching may be implemented. In FIG. 1A, an intracardiac pacemaker 100 is shown positioned in the right ventricle. FIG. 1B is a diagram of pacemaker 100. Pacemaker 100 may be a transcatheter intracardiac pacemaker adapted for implantation within the heart, e.g., within the right ventricle (RV) or within the left ventricle (LV), for sensing cardiac signals and delivering cardiac pacing pulses to the respective ventricle in which it is implanted. Pacemaker 100 is shown positioned along an endocardial wall of the RV, e.g., near the RV apex. The techniques disclosed herein, however, are not limited to the pacemaker location shown in the example of FIG. 1A and other relative locations within or along a ventricular chamber for delivering ventricular pacing pulses are possible.

Pacemaker 100 is capable of producing electrical stimulation pulses, e.g., pacing pulses, delivered to heart 8 via one or more electrodes on the outer housing of the pacemaker 100. Pacemaker 100 is configured to sense a cardiac electrical signal in the RV using the housing-based electrodes. The cardiac electrical signal may include far-field atrial events, e.g., P-waves occurring in the right atrium (RA).

Pacemaker 100 may be capable of bidirectional wireless communication with an external device 40. External device 40 is often referred to as a "programmer" because it is typically used by a physician, technician, nurse, clinician or other qualified user for programming operating parameters in pacemaker 100 as well as for retrieving device- and/or patient-related data from pacemaker 100. External device 40 may be located in a clinic, hospital or other medical facility. External device 40 may alternatively be embodied as a home monitor or a handheld device that may be used in a medical facility, in the patient's home, or another location. Operating parameters, such as sensing and therapy delivery control parameters, may be programmed into pacemaker 100 using external device 40.

External device 40 may include a microprocessor, memory, user display, user interface (such as a mouse, keyboard, or pointing device) and telemetry circuit for receiving, transmitting and processing signals sent to or received from pacemaker 100 and for enabling a clinician to view data and enter programming commands. Aspects of external device 40 may generally correspond to the external programming/monitoring unit disclosed in U.S. Pat. No. 5,507,782 (Kieval, et al.), incorporated herein by reference in its entirety.

External device 40 is configured with an external telemetry circuit for bidirectional communication with an implantable telemetry circuit (shown in FIG. 2) included in pacemaker 100. The external telemetry circuit establishes a wireless radio frequency (RF) communication link 42 with pacemaker 100 using a communication protocol that appropriately addresses pacemaker 100. Communication link 42 may be established between pacemaker 100 and external device 40 using a radio frequency (RF) link in the Medical Implant Communication Service (MICS) band, Medical Data Service (MEDS) band, BLUETOOTH® or Wi-Fi or other communication bandwidth.

In FIG. 1B, pacemaker 100 is shown to include two housing-based electrodes 162 and 164 spaced apart along the housing 150 for sensing cardiac electrical signals and delivering pacing pulses. Electrode 164 is shown as a tip electrode along a distal end 102 of pacemaker housing 150. Electrode 162 is shown as a ring electrode along a mid-portion of housing 150, for example adjacent housing proximal end 104. Housing distal end 102 is referred to as "distal" in that it is expected to be the leading end as it advanced to an implant site using a delivery tool, such as a catheter, and placed against a targeted pacing site.

Electrodes 162 and 164 form an anode and cathode pair for bipolar cardiac pacing and sensing. Electrodes 162 and 164 may be positioned on or as near as possible to respective proximal and distal ends 104 and 102 to increase the inter-electrode spacing between electrodes 162 and 164. In alternative embodiments, pacemaker 100 may include two or more ring electrodes, two tip electrodes, and/or other types of electrodes exposed along pacemaker housing 150 for delivering electrical stimulation to heart 8 and sensing cardiac electrical signals that include near-field ventricular events, e.g., R-waves attendant to ventricular depolarizations, and far-field atrial events, e.g., P-waves attendant to atrial depolarizations. Electrodes 162 and 164 may be, without limitation, titanium, platinum, iridium or alloys thereof and may include a low polarizing coating, such as titanium nitride, iridium oxide, ruthenium oxide, platinum black among others.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150, isolated from cathode tip electrode 164, may function as an electrode instead of providing a localized electrode, such as electrode 162, to serve as a return anode electrode for delivering bipolar pacing and sensing.

The housing 150 includes a control electronics subassembly 152, which houses the electronic circuitry for sensing cardiac signals, producing pacing pulses and controlling ventricular pacing pulse delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by interacting with the ventricular trabeculae or actively engaging endocardial tissue. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position. Pacemaker 100 may include a set of fixation tines as disclosed in commonly-assigned, pre-grant publication U.S. 2012/0172892 (Grubac, et al.), hereby incorporated herein by reference in its entirety.

In some examples, pacemaker 100 may include a delivery tool interface 158. Delivery tool interface 158 may be located at the proximal end 104 of pacemaker 100 and is configured to connect to a delivery device, such as a catheter, used to position pacemaker 100 at an implant location during an implantation procedure, for example within a heart chamber.

Figure 1C:
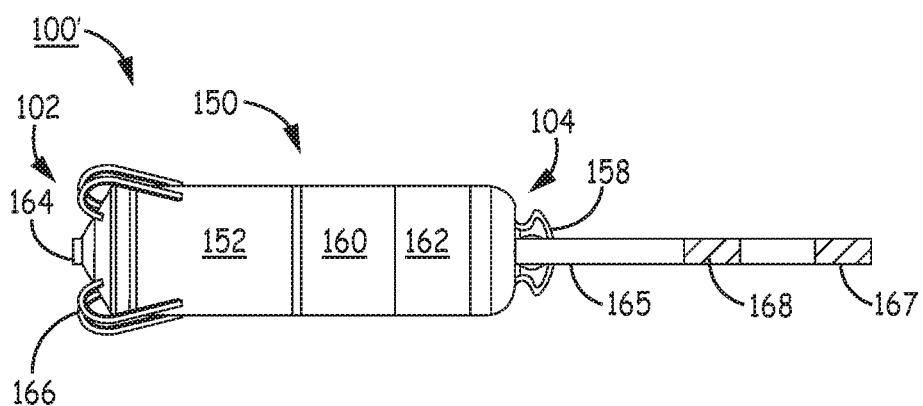
FIG. 1C is a conceptual diagram of an alternative embodiment of an intracardiac pacemaker, which may be configured to perform automatic ventricular pacing mode switching according to the techniques disclosed herein.

FIG. 1C is a conceptual diagram of an alternative embodiment of an intracardiac pacemaker 100' which may be configured to perform automatic ventricular pacing mode switching according to the techniques disclosed herein. Pacemaker 100' includes housing 150, control electronics assembly 152, battery assembly 160, fixation member 166 and housing-based electrodes 162 and 164, and may include a delivery tool interface 158 along the proximal end 104 as described above in conjunction with FIG. 1B. Pacemaker 100' is shown to include a proximal sensing extension 165 extending away from housing 150 and carrying a pair of sensing electrodes 167 and 168. The proximal sensing extension 165 may be coupled to the housing 150 for positioning a return sensing electrode 168 or 167 which may be paired with distal electrode 164 at an increased inter-electrode distance compared to housing-based electrodes 162 and 164. The increased inter-electrode distance may facilitate sensing of far-field atrial signals such as P-waves attendant to atrial depolarization.

Alternatively, electrodes 167 and 168 may form a sensing electrode pair for sensing atrial P-waves. When distal end 102 is fixed along the RV apex, sensing extension 165 may extend toward the RA thereby positioning electrodes 167 and 168 nearer the atrial tissue for sensing far-field atrial P-waves. One electrode 167 may be coupled to sensing circuitry enclosed in housing 150 via an electrical feedthrough crossing housing 150, and one electrode 168 may be coupled to housing 150 to serve as a ground electrode.

Figure 2:
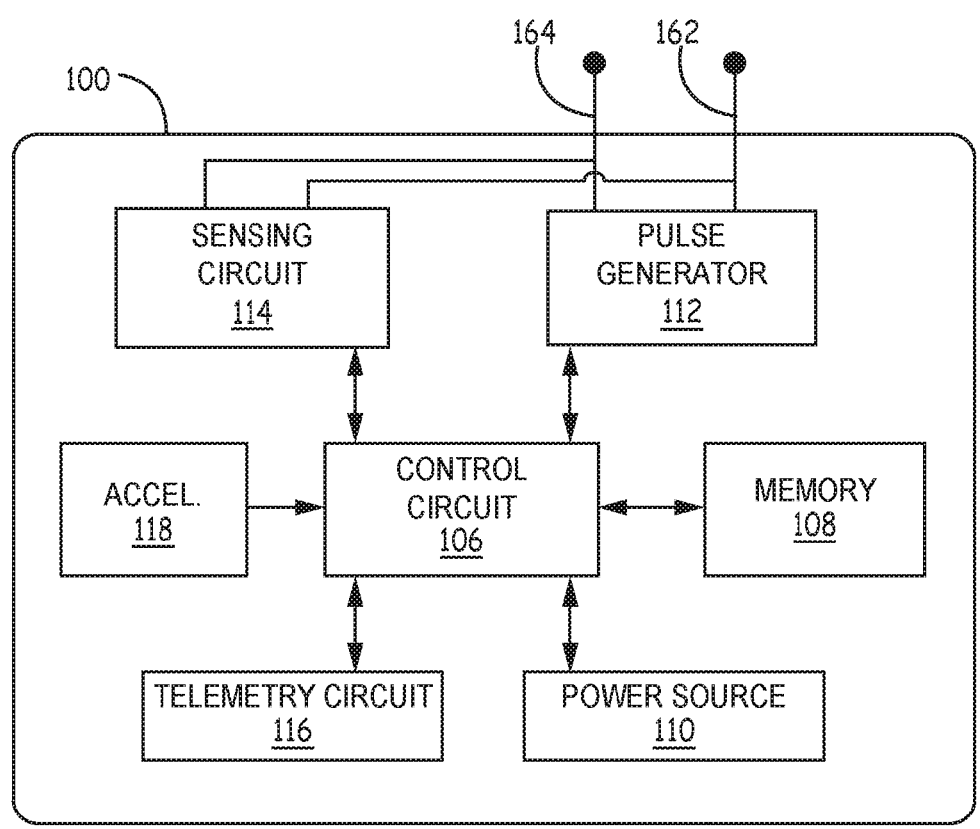
FIG. 2 is a diagram of one example configuration of the intracardiac pacemaker of FIG. 1A.

FIG. 2 is a diagram of one example configuration of pacemaker 100. Pacemaker 100 includes a control circuit 106, memory 108, power source 110, pulse generator 112, sensing circuit 114 and telemetry circuit 116. Electrodes 162 and 164 are shown coupled to pulse generator 112 and sensing circuit 114 to provide bipolar cardiac electrical signal sensing and pacing pulse delivery. It is to be understood that when pacemaker 100' is provided with a sensing extension including one or more additional sensing electrodes 167 and 168 for sensing cardiac electrical signals, the additionally available electrodes 167 and 168 are also coupled to sensing circuit 114 and may be selected via switching circuitry or coupled to a second sensing channel of sensing circuit 114 for sensing far-field atrial P-waves for use in controlling automatic ventricular pacing mode switching as described herein.

Pulse generator 112 generates electrical stimulation pulses that are delivered to heart tissue via electrodes 162 and 164. Pulse generator 112 may include one or more holding capacitors and a charging circuit to charge the capacitor(s) to a pacing pulse voltage. At controlled time intervals, the holding capacitor(s) may be discharged through an output capacitor across a pacing load, e.g., across electrodes 162 and 164. Pacing circuitry generally disclosed in U.S. Pat. No. 8,532,785 (Crutchfield), hereby incorporated herein by reference in its entirety, may be implemented in pacemaker 100 for charging a pacing capacitor to a predetermined pacing pulse amplitude under the control of control circuit 106 and delivering a pacing pulse.

Control circuit 106 may include a pace timing circuit that includes one or more timers or counters set according to programmed pacing escape intervals, which may be stored in memory 108. A pacing escape interval may be set to a V-V interval during atrial-asynchronous ventricular pacing. An atrial-asynchronous ventricular pacing mode is a non-tracking pacing mode during which ventricular pacing pulses are delivered independent of the timing of atrial activity. The V-V interval may be started when sensing circuit 114 senses an R-wave or when pulse generator 112 delivers a ventricular pacing pulse. If sensing circuit 114 senses an R-wave from the cardiac electrical signal prior to the V-V interval expiring, the V-V interval is restarted and the scheduled pacing pulse is inhibited. If the V-V interval expires without the sensing circuit 114 sensing an R-wave, the scheduled pacing pulse is delivered by pulse generator 114.

At other times, control circuit 106 may control pulse generator 112 to deliver ventricular pacing pulses in an atrial-synchronized pacing mode. An atrial-synchronized pacing mode is an atrial-tracking mode during which the timing of ventricular pacing pulses is dependent on, e.g., triggered by, sensed far-field atrial events such as P-waves from an electrical signal or atrial mechanical systole, sometimes referred to as "atrial kick" sensed from a mechanical sensor such as a motion sensor. Ventricular pacing pulses track the atrial rate. In this case, the pace timing circuit of control circuit 106 may set a timer or counter to an A-V interval when the sensing circuit 114 senses an atrial P-wave. If an R-wave is not sensed by sensing circuit 114 during the A-V interval, a ventricular pacing pulse is delivered by pulse generator 112 at the expiration of the A-V interval, synchronizing ventricular electrical activation (and ventricular mechanical systole) to the timing of the atrial activity. If an R-wave is sensed during the A-V interval, the ventricular pacing pulse may be inhibited and a new A-V interval may be restarted upon sensing the next atrial P-wave by sensing circuit 114.

Sensing circuit 114 receives a cardiac electrical signal, e.g., across electrodes 162 and 164 or across any combination of the electrodes 162, 164, 167 and 168 shown in FIG.

10. Sensing circuit 114 may include an analog filter and amplifier, an analog-to-digital converter, a digital filter, a rectifier, a sense amplifier, comparator or other event detection circuitry or components for filtering, amplifying and rectifying the cardiac electrical signal and for sensing cardiac electrical events such as far-field P-waves and near-field R-waves from the cardiac electrical signal. Sensing circuit 114 may generate a sensed event signal, e.g., a P-wave sensed event signal or an R-wave sensed event signal, in response to the cardiac electrical signal crossing a respective P-wave sensing threshold or R-wave sensing threshold.

In some examples, sensing circuit 114 may include two sensing channels, an atrial sensing channel and a ventricular sensing channel. Each channel receives a cardiac electrical signal, which may be the same signal or may be two different signals when pacemaker 100 is coupled to more than two electrodes, e.g., when sensing extension 165 is present carrying electrodes 167 and 168. The atrial sensing channel receives a cardiac electrical signal that includes far-field atrial events, e.g., far-field atrial P-waves. Both of the ventricular and atrial sensing channels may include a pre-filter and pre-amplifier, analog-to-digital convertor, filter, rectifier and a sense amplifier, comparator or other detection circuitry configured to sense respective near-field R-waves and far-field P-waves, e.g., based on a respective R-wave sensing threshold crossing and P-wave sensing threshold crossing. A P-wave sensing window or post-atrial sensing blanking period may be applied to avoid falsely sensing R-waves or T-waves as P-waves.

For example, in response to sensing an atrial event, the sensing circuit 114 may set an atrial blanking period during which atrial events are not sensed by sensing circuit 114. Since far-field atrial P-waves will generally have a small amplitude, sensing circuit 114 may be programmed to a high sensitivity for P-wave sensing. The programmed sensitivity sets the minimum P-wave sensing threshold amplitude. The P-wave sensing threshold may decay from a starting value at the expiration of the atrial blanking period to a sensing floor equal to the programmed sensitivity. Therefore, a low programmed value of the atrial sensitivity, such as 0.125 mV or 0.063 mV, corresponds to high sensitivity since very small amplitude P-waves that exceed the low sensing floor will be sensed by sensing circuit 114. In order to avoid oversensing of noise or other events as P-waves, the sensing circuit 114 may apply a relatively long atrial blanking period, e.g., at least 400 ms, at least 500 ms, or as long as 650 ms in some cases. Far-field atrial events that do occur during the atrial blanking period are not sensed by sensing circuit 114. An atrial blanking period is shown in and described in conjunction with FIG. 10

Control circuit 106 may use the sensed event signals received from sensing circuit 114 in controlling the delivery of ventricular pacing pulses, e.g., by starting and restarting pacing escape intervals in response to sensed events and inhibiting pacing pulses. As described below, control circuit 106 may determine PP intervals between consecutively sensed P-waves and/or other time intervals defined by sensed P-waves for use in automatically switching between atrial-synchronized and atrial-asynchronous ventricular pacing. Techniques for sensing P-waves by intracardiac pacemaker 100 may correspond to the methods disclosed in U.S. Pat. Publication No. 2016/0114169 Al (Demmer, et al.), incorporated herein by reference in its entirety.

Sensing of far-field atrial activity for use in controlling ventricular pacing is not limited to sensing atrial electrical activity. In some examples, pacemaker 100 may include an accelerometer 118 or other motion sensor producing a signal correlated to patient and cardiac motion. The accelerometer signal includes far-field atrial mechanical event signals. Control circuit 106 may detect an atrial mechanical event, e.g., atrial systole or correlated to the timing of atrial systole, from a signal received from accelerometer 118. Atrial mechanical events may be used instead of or in combination with atrial electrical events for determining atrial event time intervals and controlling automatic switching from atrial-synchronized to atrial-asynchronous ventricular pacing based on the sensed atrial events and associated time intervals. An intracardiac pacemaker and associated techniques for detecting atrial events from a motion signal, e.g., from an accelerometer signal, are generally disclosed in U.S. patent application Ser. No. 15/140,585 (Ghosh, et al., filed Apr. 28, 2016), incorporated herein by reference in its entirety.

Control circuit 106 may be a microprocessor-based controller that communicates with memory 108, pulse generator 112, sensing circuit 114 and telemetry circuit 116, and accelerometer 118 for example via a data bus. Power source 110 provides power to each of the other components of pacemaker 100 as required. Control circuit 106 may execute power control operations to control when various components are powered to perform various pacemaker functions and when they are powered down to conserve energy. Power source 110 may include one or more energy storage devices, such as one or more rechargeable or non-rechargeable batteries. Power source 110 provides power to pulse generator for charging pacing capacitor(s) for generating pacing pulses.

Circuitry represented by the block diagram shown in FIG. 2 and other IMD block diagrams presented herein may include any discrete and/or integrated electronic circuit components that implement analog and/or digital circuits capable of producing the functions attributed to pacemaker 100 or another IMD performing the automatic ventricular pacing mode switching as described herein. The functions attributed to pacemaker 100 or other IMDs presented herein may be embodied as one or more processors, hardware, firmware, software, or any combination thereof. Control circuit 106 may include any one or more of a microprocessor, a controller, a digital signal processor (DSP), an application specific integrated circuit (ASIC), a field-programmable gate array (FPGA), state machine, or equivalent discrete or integrated logic circuitry.

Depiction of different features of pacemaker 100 as discrete circuits or components is intended to highlight different functional aspects and does not necessarily imply that such circuits must be realized by separate hardware or software components. Rather, functionality associated with one or more circuits may be performed by separate hardware or software components, or integrated within common or separate hardware or software components, which may include combinational or sequential logic circuits, state machines, memory devices, etc.

Memory 108 may include computer-readable instructions that, when executed by control circuit 106, cause control circuit 106 to perform various functions attributed throughout this disclosure to pacemaker 100. The computer-readable instructions may be encoded within memory 108. Memory 108 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Pacemaker 100 may include a telemetry circuit 116 having a transceiver and antenna for bidirectional communication with external device 40. Sensing control parameters and pacing control parameters may be received from external device 40 via telemetry circuit 116 and passed to control circuit 106 or stored in memory 108 for retrieval by control circuit 106 as needed.

Figure 3:
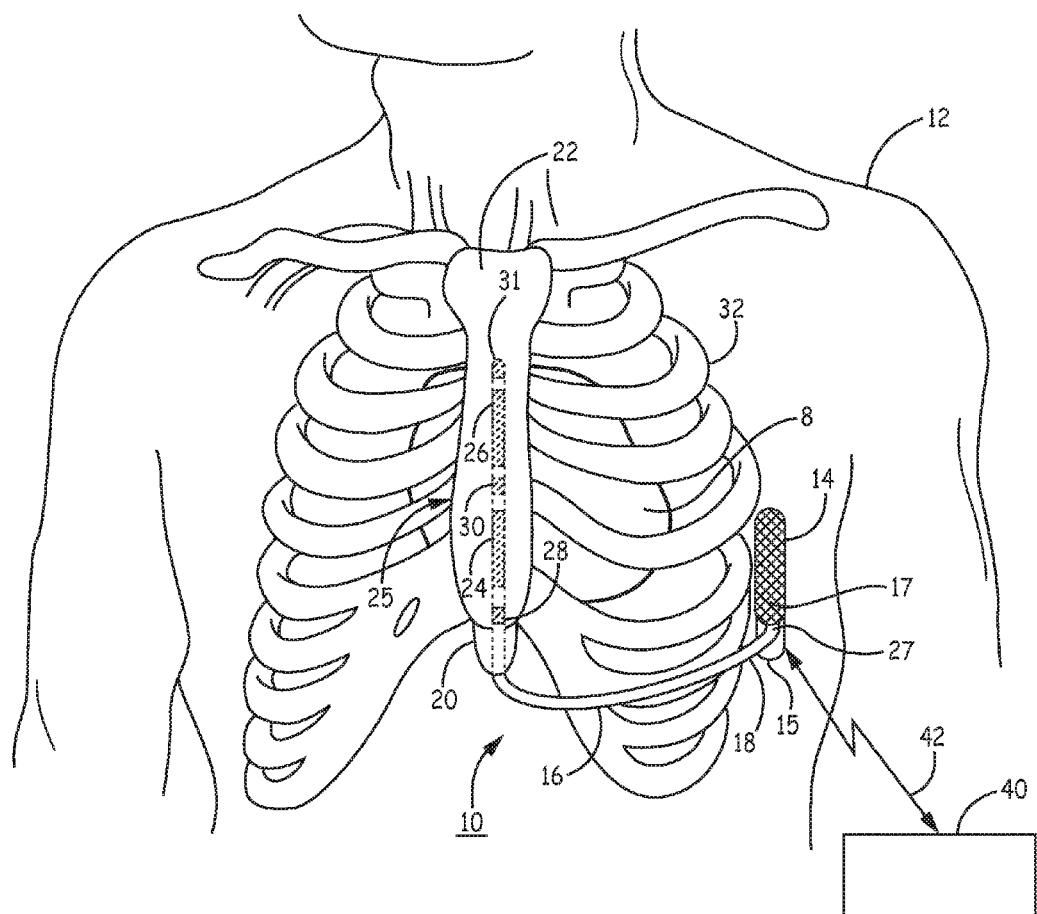
FIG. 3 is a conceptual diagram of an extra-cardiovascular ICD system according to one example.

FIG. 3 is a conceptual diagram of an extra-cardiovascular implantable cardioverter defibrillator (ICD) system 10 according to one example. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein for controlling switching between atrial-synchronized and atrial-asynchronous ventricular pacing may be implemented in an extra-cardiovascular ICD or other extra-cardiovascular IMD system configured to sense cardiac signals and deliver pacing pulses to the patient's heart 8 via extra-cardiovascular electrodes.

FIG. 3 is a front view of a patient 12 implanted with extra-cardiovascular ICD system 10 including ICD 14 connected to an extra-cardiovascular electrical stimulation and sensing lead 16. ICD system 10 may be capable of providing defibrillation and/or cardioversion shocks and pacing pulses to heart 8.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a can electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes and for sensing cardiac electrical signals including far-field atrial events in conjunction with lead-based electrodes. In other instances, the housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIG. 3, the distal portion 25 of lead 16 includes defibrillation electrodes 24 and 26 and pace/sense electrodes 28, 30 and 31. In some instances, defibrillation electrodes 24 and 26 are coupled to electrically isolated conductors, and ICD 14 may include switching mechanisms to allow electrodes 24 and 26 to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to low voltage pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a pacing electrode vector for delivering extra-cardiovascular pacing pulses, such as ventricular pacing pulses in an atrial tracking or non-tracking pacing mode, and/or in a sensing vector used to sense cardiac electrical signals including far-field atrial events for controlling ventricular pacing and for detecting ventricular tachyarrhythmias for controlling high voltage therapies.

Electrodes 28, 30 and 31 are relatively smaller surface area electrodes for delivering low voltage pacing pulses and for sensing cardiac electrical signals. Electrodes 28, 30 and 31 are referred to as pace/sense electrodes because they are generally configured for use in low voltage applications, e.g., used as either a cathode or anode for delivery of pacing pulses and/or sensing of cardiac electrical signals. In some instances, electrodes 28, 30 and 31 may provide only pacing functionality, only sensing functionality or both.

Electrode 28 is shown proximal to defibrillation electrode 24, and electrode 30 is located between defibrillation electrodes 24 and 26. A third pace/sense electrode 31 may be located distal to defibrillation electrode 26. Electrodes 28 and 30 are illustrated as ring electrodes, and electrode 31 is illustrated as a hemispherical tip electrode in the example of FIG. 3. However, electrodes 28, 30 and 31 may comprise any of a number of different types of electrodes, including ring electrodes, short coil electrodes, hemispherical electrodes, directional electrodes, segmented electrodes, or the like, and may be positioned at any position along the distal portion 25 of lead 16 and are not limited to the positions shown. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly beneath sternum 22. Extra-cardiovascular lead 16 of system 10 is implanted at least partially underneath sternum 22 of patient 12. At a location near xiphoid process 20, lead 16 may bend or turn and extend superiorly within the anterior mediastinum in a substernal position. A lead implanted such that the distal portion 25 is substantially within anterior mediastinum may be referred to as a "substernal lead."

In the example illustrated in FIG. 3, lead 16 is located substantially centered under sternum 22. In other instances, however, lead 16 may be implanted such that it is offset laterally from the center of sternum 22. Lead 16 may angle laterally such that distal portion 25 of lead 16 is underneath/below the ribcage 32 in addition to or instead of sternum 22. The distal portion 25 of lead 16 may be offset laterally from sternum 22, e.g., to the right or left of sternum 22, angled laterally from sternum 22 toward the left or the right, or the like. In other examples, the distal portion 25 of lead 16 may be implanted in other extra-cardiovascular, intra-thoracic locations, including the pleural cavity or around the perimeter of and adjacent to but typically not within the pericardium 38 of heart 8.

Electrical conductors (not illustrated) extend through one or more lumens of the elongated lead body 18 of lead 16 from the lead connector at the proximal lead end 27 to respective electrodes 24, 26, 28, 30 and 31 located along the distal portion 25 of the lead body 18. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The respective conductors electrically couple the electrodes 24, 26, 28, 30 and 31 to circuitry, such as a therapy delivery circuit and/or a sensing circuit as described below, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28, 30 and 31 and transmit sensed electrical signals from one or more of defibrillation electrodes 24 and 26 and/or pace/sense electrodes 28, 30 and 31 to the sensing circuit within ICD 14.

ICD 14 may obtain electrical signals corresponding to electrical activity of heart 8 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing vector that includes one or both defibrillation electrodes 24 and/or 26, e.g., between electrodes 24 and 26 or one of electrodes 24 or 26 in combination with one or more of electrodes 28, 30, 31, and/or the housing 15.

ICD 14 analyzes the cardiac electrical signals received from one or more of the sensing vectors to monitor for abnormal rhythms, such as bradycardia, ventricular tachycardia (VT) or ventricular fibrillation (VF). ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting bradycardia or a tachyarrhythmia (e.g., VT or VF). ICD 14 may deliver anti-tachycardia pacing (ATP) in response to VT detection, and in some cases may deliver ATP prior to a cardioversion/defibrillation (CV/DF) shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15.

Ventricular pacing pulses may be delivered using an extra-cardiovascular pacing electrode vector selected from any of electrodes 24, 26, 28, 30, 31 and/or housing 15. Ventricular pacing mode may be controlled based on far-field atrial events sensed using a sensing vector selected from electrodes 24, 26, 28, 30 31 and/or housing 15. The pacing electrode vector may be different than the sensing electrode vector. In one example, cardiac electrical signals are sensed between pace/sense electrodes 28 and 30 and/or between one of pace/sense electrodes 28 or 30 and housing 15, and pacing pulses are delivered between pace/sense electrode 30 used as a cathode electrode and defibrillation electrode 24 used as a return anode electrode. In other examples, pacing pulses may be delivered between pace/sense electrode 28 and either (or both) defibrillation electrodes 24 or 26 or between defibrillation electrode 24 and defibrillation electrode 26. These examples are not intended to be limiting, and it is recognized that other sensing electrode vectors and pacing electrode vectors may be selected according to individual patient need. The techniques for controlling pacing mode switching are not limited by pacing electrode vector and electrode positions. Various examples of extra-cardiovascular IMD systems and associated techniques for delivering extra-cardiovascular pacing pulses are described in U.S. patent application Ser. No. 14/957,651 (Thompson-Nauman, et al.), provisionally-filed U.S. Patent Application No. 62/262,499 (Anderson, et al.) and provisionally-filed U.S. Patent Application No. 62/262,412 (Anderson, et al.), all of which are incorporated herein by reference in their entirety.

FIG. 3 is illustrative in nature and should not be considered limiting of the practice of the techniques in an extra-cardiovascular ICD system as disclosed herein. In other examples, extra-cardiovascular lead 16 may include more or fewer electrodes than the number of electrodes shown in FIG. 3, and the electrodes may be arranged along the lead 16 in different configurations than the particular arrangement shown in FIG. 3. Various example configurations of extra-cardiovascular leads and electrodes and dimensions that may be implemented in conjunction with the extra-cardiovascular pacing techniques disclosed herein are described in U.S. Publication No. 2015/0306375 (Marshall, et al.) and U.S. Publication No. 2015/0306410 (Marshall, et al.), both of which are incorporated herein by reference in their entirety. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in U.S. Pat. Publication No. 2016/0158567, (Marshall, et al.), incorporated herein by reference in its entirety.

In other examples, the distal portion 25 may extend subcutaneously or submuscularly over the ribcage and/or sternum or along other subcutaneous or submuscular paths. For instance, as described with respect to FIG. 5, the distal portion 25 of lead 16 may be implanted outside the thorax, over the sternum/ribcage rather than in the substernal space as shown in FIG. 3. The path of extra-cardiovascular lead 16 may depend on the location of ICD 14, the arrangement and position of electrodes carried by the lead distal portion 25, and/or other factors. For example, ICD 14 is shown implanted subcutaneously on the left side of patient 12 along the ribcage 32, but in other examples ICD 14 may be implanted between the left posterior axillary line and the left anterior axillary line of patient 12 or other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally.

As generally described above in conjunction with FIG. 1A and pacemaker 100, an external device 40 may be used to establish a telemetric communication link 42 with ICD 14 to retrieve data from ICD 14 and to program operating parameters and algorithms in ICD 14 for controlling ICD functions. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

Figure 4:
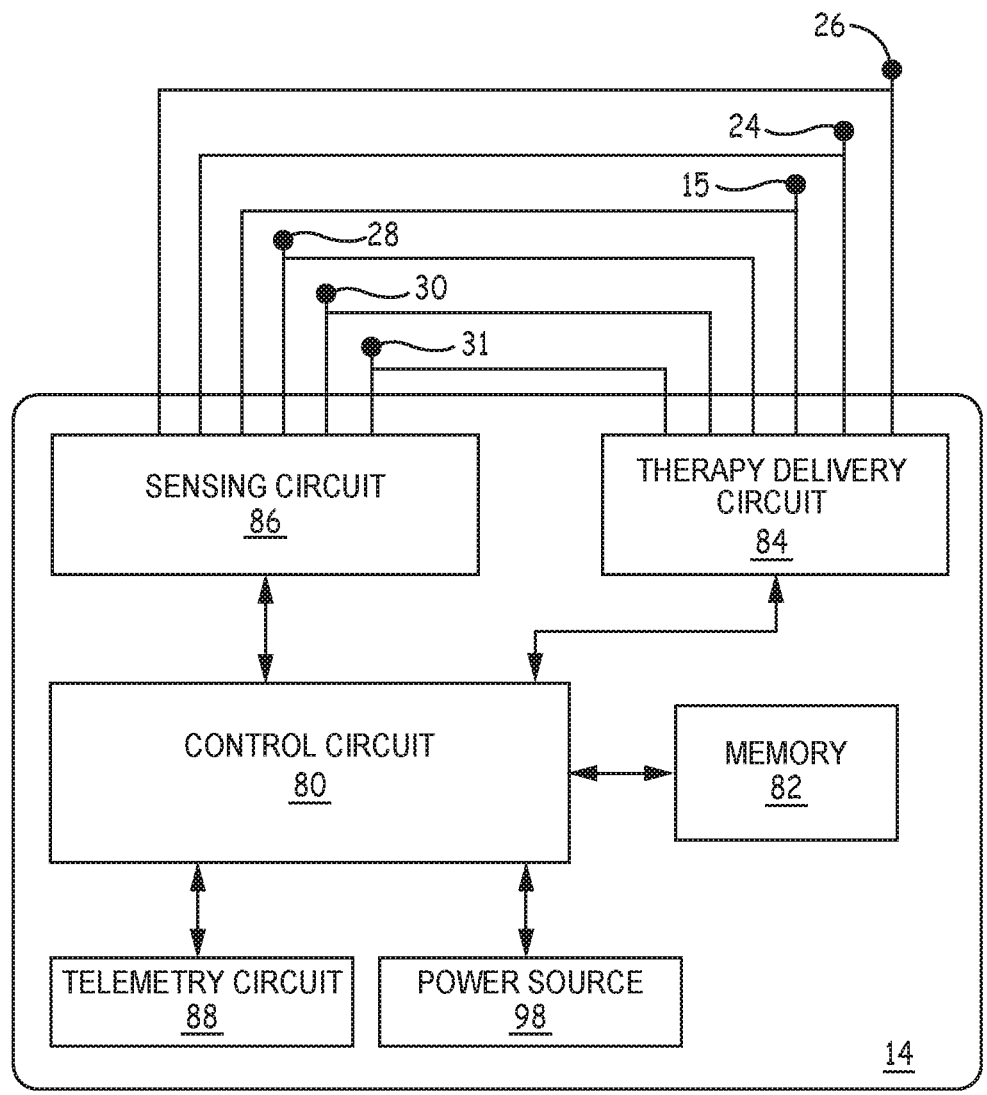
FIG. 4 is a schematic diagram of the ICD of FIG. 3 according to one example.

FIG. 4 is a schematic diagram of ICD 14 according to one example. The electronic circuitry enclosed within housing 15 (shown schematically as an electrode in FIG. 4) includes software, firmware and hardware that cooperatively monitor cardiac electrical signals, determine when an electrical stimulation therapy is necessary, and deliver therapies as needed according to programmed therapy delivery algorithms and control parameters. The software, firmware and hardware are configured to detect tachyarrhythmias and deliver anti-tachyarrhythmia therapy, e.g., detect ventricular tachyarrhythmias and in some cases discriminate VT and VF for determining when ATP or CV/DF shocks are required. According to the techniques disclosed herein, the software, firmware and hardware are further configured to sense far-field atrial events and control ventricular pacing mode switching based on the sensed atrial events. Ventricular pacing pulses are delivered according to the selected pacing mode.

ICD 14 includes a control circuit 80, memory 82, therapy delivery circuit 84, sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 4, but are not shown for the sake of clarity. For example, power source 98 may be coupled to a low voltage (LV) charging circuit and to a high voltage (HV) charging circuit included in therapy delivery circuit 84 for charging low voltage and high voltage capacitors, respectively, included in therapy delivery circuit 84 for producing respective low voltage pacing pulses, such as bradycardia pacing, post-shock pacing or ATP pulses, or for producing high voltage pulses, such as CV/DF shock pulses. In some examples, high voltage capacitors are charged and utilized for delivering pacing pulses, e.g., for ATP, post-shock pacing or other ventricular pacing pulses, instead of low voltage capacitors. Power source 98 is also coupled to components of sensing circuit 86, such as sense amplifiers, analog-to-digital converters, switching circuitry, etc. as needed.

The functional blocks shown in FIG. 4 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern IMD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as components is intended to highlight different functional aspects and does not necessarily imply that such components must be realized by separate hardware or software components. Rather, functionality associated with one or more components may be performed by separate hardware, firmware or software components, or integrated within common hardware, firmware or software components.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 and 31 and the housing 15, which may function as a common or ground electrode or as an active can electrode for delivering CV/DF shock pulses or cardiac pacing pulses.

Sensing circuit 86 may be selectively coupled to electrodes 28, 30, 31 and/or housing 15 in order to monitor electrical activity of the patient's heart. Sensing circuit 86 may additionally be selectively coupled to defibrillation electrodes 24 and/or 26 for use in a sensing electrode vector. Sensing circuit 86 may include multiple sensing channels for receiving cardiac electrical signals from two or more sensing electrode vectors selected from the available electrodes 24, 26, 28, 30, 31 and housing 15. For example, sensing circuit 86 may include a ventricular sensing channel configured to sense ventricular R-waves from a received cardiac electrical signal and an atrial sensing channel configured to sense far-field atrial P-waves from the same or a difference cardiac electrical signal. Sensing circuit 86 may include switching circuitry for selecting which of electrodes 24, 26, 28, 30, 31 and housing 15 are coupled to the one or more sensing channels. Switching circuitry may include a switch array, switch matrix, multiplexer, or any other type of switching device suitable to selectively couple components of sensing circuit 86 to selected electrodes.

Cardiac event detection circuitry within sensing circuit 86 may include one or more sense amplifiers, filters, rectifiers, threshold detectors, comparators, analog-to-digital converters (ADCs), or other analog or digital components configured to filter and amplify a cardiac electrical signal received from a selected sensing electrode vector and sense cardiac events, e.g., P-waves and R-waves. A cardiac event sensing threshold may be automatically adjusted by sensing circuit 86 under the control of control circuit 80, based on timing intervals and sensing threshold values determined by control circuit 80, stored in memory 82, and/or controlled by hardware of control circuit 80 and/or sensing circuit 86.

Upon detecting a cardiac event based on a sensing threshold crossing, sensing circuit 86 may produce a sensed event signal, such as a P-wave sensed event signal or an R-wave sensed event signal, which is passed to control circuit 80. Sensing circuit 86 may be configured to sense far-field atrial P-waves from a cardiac signal using a high sensitivity and relatively long atrial blanking period as described above in conjunction with FIG. 2. The sensed event signals produced by sensing circuit 86 are used by control circuit 80 to control the timing of pacing pulses delivered by therapy delivery circuit 84. As described below in conjunction with FIGS. 8 and 9, control circuit 80 may determine atrial cycle lengths, e.g., PP intervals, as the time intervals between consecutively sensed P-waves. Other atrial time intervals may be determined between the expiration of the atrial blanking period and the next atrial sensed event. These atrial cycle lengths and atrial time intervals may be used for determining when ventricular pacing pulses are delivered synchronized to atrial events and when ventricular pacing pulses are delivered in a non-tracking, atrial-asynchronous pacing mode.

R-wave sensed event signals generated by sensing circuit 86 may cause control circuit 80 to withhold a scheduled ventricular pacing pulse and/or start a V-V pacing escape interval. R-wave sensed event signals may also be used by control circuit 80 for determining RR intervals (RRIs) for detecting tachyarrhythmia and determining a need for therapy. An RRI is the time interval between consecutively sensed R-waves and may be determined between consecutive R-wave sensed event signals received from sensing circuit 86. For example, control circuit 80 may include a timing circuit for determining RRIs between consecutive R-wave sensed event signals received from sensing circuit 86 and PP intervals between consecutive P-wave sensed event signals. R-wave and P-wave sensed event signals are also used for controlling various timers and/or counters used to control the timing of therapy delivery by therapy delivery circuit 84. The timing circuit may additionally set time windows such as morphology template windows, morphology analysis windows, P-wave sensing windows, blanking periods, R-wave sensing windows, pacing escape intervals including A-V and V-V intervals or perform other timing related functions of ICD 14 including synchronizing cardioversion shocks or other therapies delivered by therapy delivery circuit 84 with sensed cardiac events.

Therapy delivery circuit 84 includes charging circuitry, one or more charge storage devices, such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when ATP or other cardiac pacing pulses are delivered. For example, the timing circuit of control circuit 80 may include programmable digital counters set by a microprocessor of the control circuit 80 for controlling the basic time intervals associated with ventricular pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

During pacing, escape interval counters within control circuit 80 are reset upon sensing of R-waves as indicated by signals from sensing circuit 86. In accordance with the selected mode of pacing, pacing pulses are generated by a pulse output circuit of therapy delivery circuit 84 when an escape interval counter expires. The pace output circuit is coupled to the desired pacing electrodes via a switch matrix for discharging one or more capacitors across the pacing load. The escape interval counters are reset upon generation of pacing pulses, and thereby control the basic timing of cardiac pacing functions. The durations of the escape intervals are determined by control circuit 80 via a data/address bus. The value of the count present in the escape interval counters when reset by sensed R-waves can be used to measure RRIs for detecting the occurrence of a tachyarrhythmia.

Memory 82 may include read-only memory (ROM) in which stored programs controlling the operation of the control circuit 80 reside. Memory 82 may further include random access memory (RAM) or other memory devices configured as a number of recirculating buffers capable of holding a series of measured PP intervals, RR intervals, counts or other data for analysis by control circuit 80 for controlling therapy delivery.

Control parameters utilized by control circuit 80 for detecting cardiac rhythms and controlling therapy delivery may be programmed into memory 82 via telemetry circuit 88. Telemetry circuit 88 includes a transceiver and antenna for communicating with external device 40 (shown in FIG. 3) using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 5:
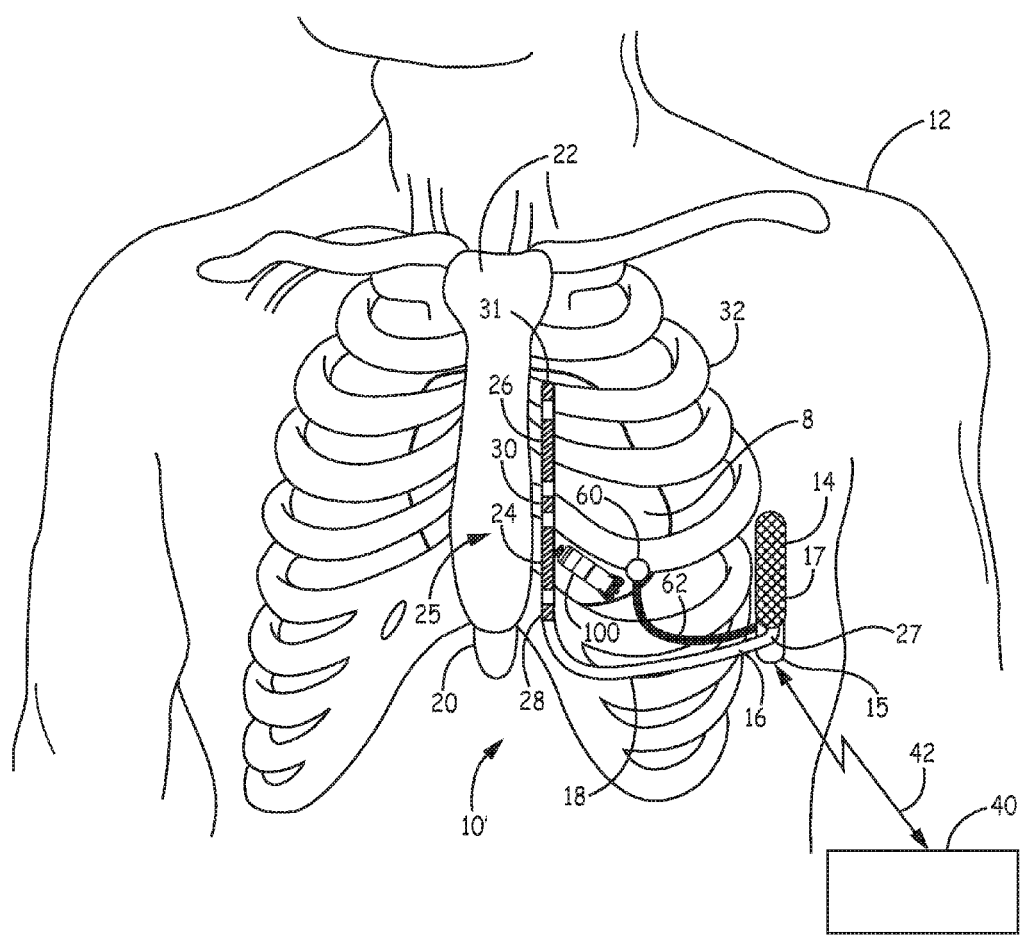
FIG. 5 is a conceptual diagram of another example of an IMD system which may be configured to deliver ventricular pacing to a patient's heart.

FIG. 5 is a conceptual diagram of another example of an IMD system 10' which may be configured to deliver ventricular pacing to a patient's heart 8. IMD system 10' includes extra-cardiovascular ICD 14 coupled to extra-cardiovascular lead 16 and intracardiac pacemaker 100. The distal portion 25 of lead 16 is shown extending outside the thoracic cavity, substantially parallel to sternum 22 in FIG. 5, but may alternatively be positioned in any of the substernal or supra-sternal configurations described above in conjunction with FIG. 3.

IMD system 10' is configured as a triggered pacing system in which ICD 14 senses cardiac electrical signals for determining the timing of ventricular pacing pulses and transmits a trigger signal to intracardiac pacemaker 100 for triggering pacemaker 100 to deliver the appropriately timed ventricular pacing pulse.

In this example, a trigger signal emitting device 60 is carried by a separate lead 62 coupled to ICD 14 and positioned extrathoracically, e.g., along an intercostal space, to direct a trigger signal toward pacemaker 100 through the intercostal space and intervening muscle, blood, myocardial tissue, etc. Trigger signal emitting device 60 is capable of receiving an electrical control signal from ICD 14 conducted along lead 62. Upon receipt of the control signal, emitting device 60 emits a trigger signal to cause pacemaker 100 to deliver a ventricular pacing pulse.

A dedicated lead 62 carrying emitting device 60 may be provided to position emitting device 60 at an optimal location for transmitting a trigger signal to pacemaker 100. An optimal location is a location of emitting device 60 relative to pacemaker 100 that allows a trigger signal to reach pacemaker 100 with adequate signal intensity and signal-to-noise ratio that it is reliably detected by pacemaker 100. Depending on the type of trigger signal being transmitted, a trigger signal path between emitting device 60 and pacemaker 100 may include tissues that attenuate the trigger signal through absorption, scattering or reflection of the signal. The location of emitting device 60 is selected such that signal losses along the path do not reduce the intensity of the trigger signal below a threshold level that is detectable by pacemaker 100.

In some examples, emitting device 60 may have its own battery, which may be rechargeable, such that the power required by ICD 14 for sensing and therapy delivery functions and the power required for trigger signal emission is distributed across two devices and two (or more) batteries or other power sources. Emitting device 60 may alternatively be embodied as a leadless device capable of receiving a wireless control signal from ICD 14 to cause trigger signal emission. For example, emitting device 18 may include an RF receiver for receiving a wireless RF control signal from ICD 14 transmitted by the ICD telemetry circuit 88.

Emitting device 60 carried by a dedicated lead 60, or a leadless emitting device, may be positioned at an optimal location for transmitting a trigger signal to pacemaker 100 without limitations associated with optimal positioning of electrodes 24, 26, 28 and 30, and 31 for sensing cardiac electrical signals and delivering or electrical stimulation therapies. A leadless emitting device may be implanted at a desired site without requiring lead tunneling. The emitting device 60 may act as a relay device for transmitting a pacing timing control signal from ICD 14 to pacemaker 100 by converting the pacing timing control signal to a trigger signal that is transmitted to and detected by pacemaker 100. In other examples, the trigger signal emitting device may be incorporated within ICD housing 15, connector assembly 17, or along lead 16. Various examples of a triggered pacing system in which the presently disclosed techniques for controlling automatic switching of a ventricular pacing mode may be implemented are generally described in U.S. Pat. Publication No. 2015/0321012 (Cinbas, et al.), U.S. Publication. No. 2015/0321016 A1 (O'Brien, et al.), and U.S. Publication No. 2015/0321011 (Carney, et al.), all of which are incorporated herein by reference in their entirety.

Figure 6:
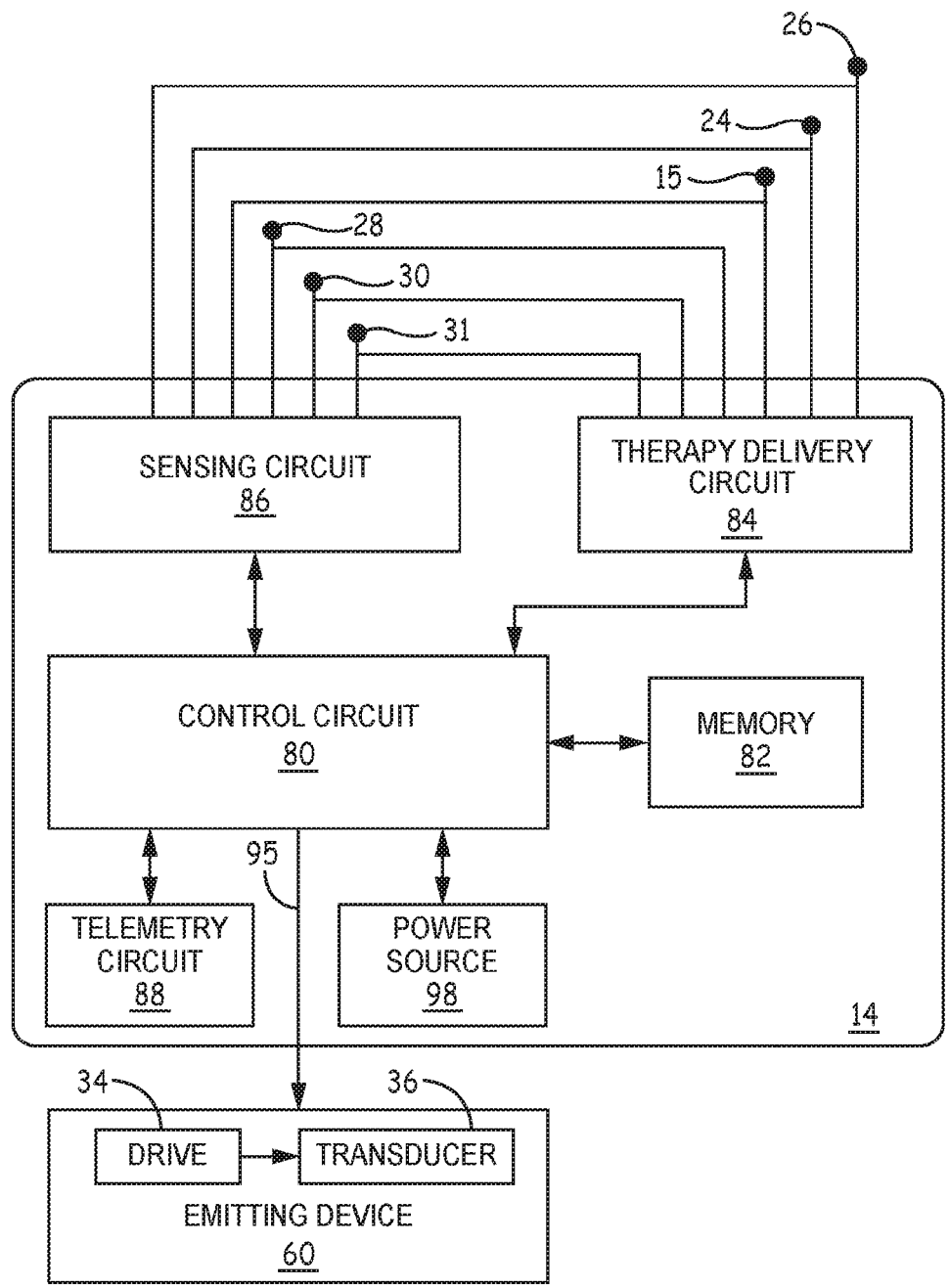
FIG. 6 is a schematic diagram of the ICD of FIG. 5 and a trigger signal emitting device.

FIG. 6 is a schematic diagram of ICD 14 and trigger signal emitting device 60. Control circuit 80 passes a timing control signal 95 to emitting device 60 in response to a pacing escape interval expiring, which may be an A-V interval set in response to a far-field P-wave sensed by sensing circuit 86 during atrial-synchronized ventricular pacing or a V-V interval set in response to an R-wave sensed by sensing circuit 86 or a delivered ventricular pacing pulse during atrial-asynchronous ventricular pacing. As indicated above, emitting device 60 may be electrically coupled to ICD 14 via a dedicated lead 62 or alternatively carried by lead 16, in which case control signal 95 may be conducted to emitting device 60 via an electrical conductor extending through lead 62 or lead 16. In other examples, emitting device 60 may be incorporated in housing 15 or connector assembly 17 in which case control signal 95 is passed to emitting device 60 via an electrical conductor coupling emitting device 60 to control circuit 80. In still other examples, emitting device 60 may be a wireless device including a receiver and antenna for receiving a control signal 95 as a wireless signal transmitted from control circuit 80 via telemetry circuit 88. In some examples, when emitting device 60 is a wireless device, control signal 95 may be transmitted from ICD 14 to emitting device 60 using tissue conductance communication (TCC). Communication between two implanted medical devices using tissue conductance is generally disclosed in U.S. Pat. No. 4,987,897 (Funke), incorporated herein by reference in its entirety. The control signal 95 may be referred to as a pacing control timing signal because it causes pacemaker 100 to deliver a pacing pulse to a heart chamber. The control signal 95 is relayed to pacemaker 100 via emitting device 60.

Trigger signal emitting device 60 includes a drive signal circuit 34 that receives the control signal 95. Drive signal circuit 34 passes an electrical signal to transducer 36 to enable transducer 36 to emit the trigger signal. Transducer 36 may be an optical transducer producing an optical trigger signal or an acoustical transducer producing an acoustical trigger signal.

Transducer 36 may be embodied as one or more transducers configured to emit sound or light, for example, upon receiving a drive signal from circuit 34. Transducer 36 may include any combination of one or more of a ceramic piezoelectric crystal, a polymer piezoelectric crystal, capacitive micromachined ultrasonic transducer (CMUT), piezoelectric micromachined ultrasonic transducer (PMUT), or other ultrasonic transducer, a light emitting diode (LED), a vertical cavity surface emitting laser (VCSEL) or other light source having a high quantum efficiency at a selected light wavelength. Transducer 36 may include multiple transducers arranged in an array and/or configured to emit signals in multiple directions from emitting device 60 to promote reception of the trigger signal by pacemaker 100 despite shifting, rotation or other changes of the relative orientations of emitting device 18 and pacemaker 100 with respect to each other. The multiple transducers may be selectable by drive circuit 34 such that a single one or combination of transducers is selected that produces the best signal-to-noise ratio at a receiving transducer of pacemaker 100.

The transducer 36 is configured to emit a trigger signal at an amplitude and frequency that is detectable by a receiving transducer of pacemaker 100, after attenuation by body tissues along the pathway between the transducer 36 and the pacemaker 100. In one example, transducer 36 is configured to emit sounds in the range of approximately 40 kHz to over 1 MHz. An optical trigger signal may be emitted with a wavelength greater than approximately 1000 nm. An RF signal can be radiated from an antenna at frequencies between 400 MHz and 3 GHz. The frequency of the trigger signal is selected in part based on the types and thicknesses of body tissues encountered along the signal pathway.

In some examples, emitting device 60 may include electrodes for transmitting the trigger signal as a tissue conductance communication signal or a tissue conductance communication signal may be transmitted using electrodes carried by lead 16. In still other examples, the drive signal circuit 34 is coupled to an antenna for transmitting the trigger signal as an RF signal to pacemaker 100. When the trigger signal is transmitted as an RF trigger signal, emitting device 60 may be optional and control circuit 80 may pass control signal 95 directly to telemetry circuit 88 for transmitting the trigger signal.

In this example, control circuit 80 is configured to monitor far-field P-waves and R-waves for controlling the timing of control signal 95 according to a selected ventricular pacing mode. As described below in conjunction with FIGS. 8 and 9, control circuit 80 may determine PP intervals based on P-wave sensed events signals received from sensing circuit 86. Control circuit 80 compares the PP intervals to mode-switching criteria and switches between an atrial-synchronized ventricular pacing mode and an atrial-asynchronous pacing mode based on the PP intervals. Control signal 95 causes emitting device 60 to transmit a trigger signal to pacemaker 100 to control ventricular pacing by pacemaker 100 according to the selected pacing mode.

Figure 7:
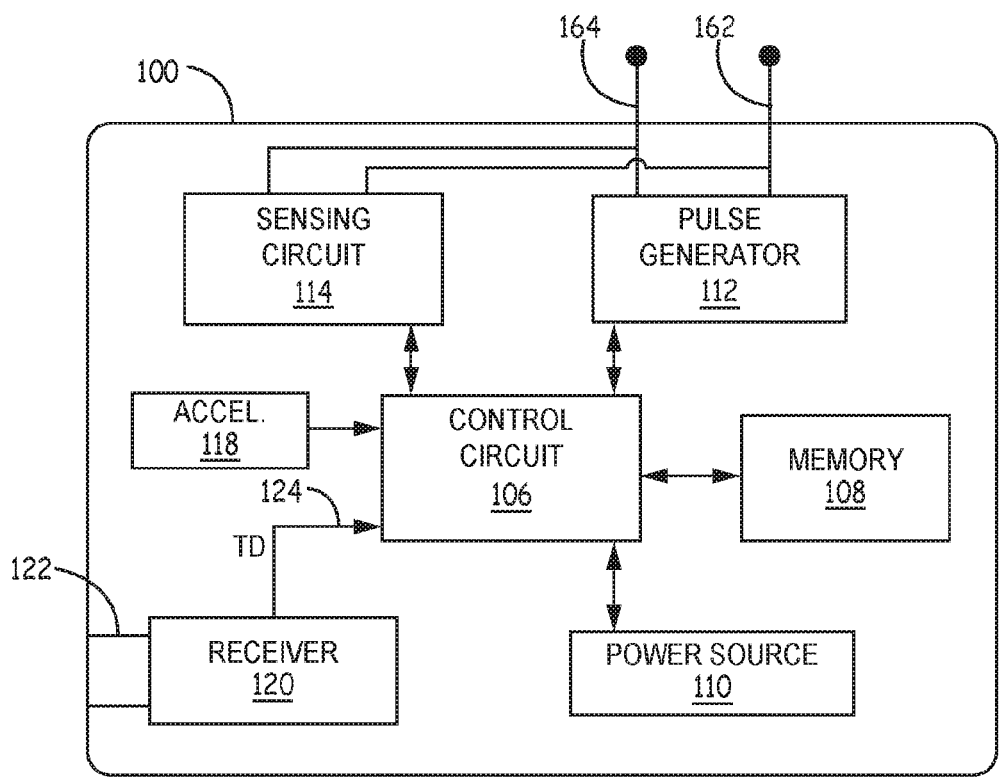
FIG. 7 is a functional block diagram of another example configuration of an intracardiac pacemaker including a receiver for receiving a trigger signal from the emitting device of FIG. 5.

FIG. 7 is a functional block diagram of another example configuration of pacemaker 100 including a receiver 120 for receiving a trigger signal from emitting device 60. Pacemaker 100 includes control circuit 106, memory 108, power source 110 and pulse generator 112 as described above in conjunction with FIG. 3. Pacemaker 100 may also include sensing circuit 114, accelerometer 118 and telemetry circuit 116 as described above. Pacemaker 100 may be configured to generate pulsing pulses using power supplied by power source 110 in response to receiving a trigger signal by receiver 120, transmitted by emitting device 60.

In other examples, an on-board power source 110 is optional. When an on-board power source 110 is not included in pacemaker 100 for supplying power to pulse generator 112 required for delivering pacing pulses, receiver 120 may act as a power-harvesting device. Power may be harvested from a trigger signal received from emitting device 60 and used for producing the pacing pulse delivered by pulse generator 112. Examples of power-harvesting techniques in an IMD system in which the techniques disclosed herein may be implemented are generally disclosed in U.S. Pat. Publication No. 2013/0282073 (Cowan, et al.).

Pacemaker 100 may rely only on receiving trigger signals by receiver 120 for controlling timing of pacing pulses such that sensing circuit 114 and accelerometer 118 are optional. In other examples, sensing circuit 114 and/or accelerometer 118 may be included for monitoring a cardiac electrical signal and/or a motion signal, respectively, for use in controlling ventricular pacing delivered by IMD system 10'.

As described above, pulse generator 112 generates electrical stimulation pulses that are delivered to heart tissue via electrodes 162 and 164. Control circuit 106 controls pulse generator 112 to deliver a stimulation pulse in response to receiving a trigger detect (TD) signal 124 from receiver 120. Pulse generator 112 may include one or more holding capacitors and a charging circuit to charge the capacitor(s) to a pacing pulse voltage. The pacing holding capacitor may be charged to the pacing pulse voltage while control circuit 106 waits for a trigger detect signal 124 from receiver 120. Upon detecting the trigger signal, the holding capacitor is coupled to pacing electrodes 162, 164 to discharge the holding capacitor voltage, typically through an output capacitor, and thereby deliver the pacing pulse. Alternatively, detection of the trigger signal initiates holding capacitor charging and when a predetermined pacing pulse voltage is reached, the pulse is delivered.

In other embodiments, pulse generator 112 may be configured to be enabled to deliver a stimulation pulse directly by an input signal received from receiver 120. For example, a switch responsive to a trigger detect signal 124 produced by receiver 120 may enable pulse generator 112 to deliver a stimulation pulse to a targeted tissue via electrodes 162 and 164. Pulse generator 112 may include a switch that connects power source 110 to pacing electrodes 162 and 164 to deliver the pacing pulse. The switch is opened by trigger detect signal 124 or by a control signal from control circuit 106, and power source 110 delivers energy to pulse generator 112 for generating a pacing pulse.

Receiver 120 may receive trigger signals through a coupling member 122. Coupling member 122 may be an acoustical or optical coupling member that improves transmission, e.g., by reducing signal losses, of the trigger signal from the surrounding tissue to receiver 120. Receiver 120 may include one or more receiving transducers, which may be mounted directly along an inner surface of coupling member 122, e.g., for receiving sound waves or light. The trigger signal causes a receiving transducer to produce a voltage signal which may be passed to a comparator included in receiver 120 (or control circuit 106) for comparison to a trigger signal detection threshold. If the voltage signal produced by the receiving transducer is greater than the detection threshold, a trigger detect signal 124 is passed to control circuit 106 (or directly to pulse generator 112), to cause pacing pulse delivery. Receiver 120 may be "tuned" to detect an acoustical or optical trigger signal of a predetermined signal frequency or bandwidth.

Control circuit 106 may control pulse generator 112 to deliver a pacing pulse according to programmed therapy delivery control parameters such as pulse amplitude, pulse width, etc., which may be stored in memory 108. In some examples, pulse generator 112 is enabled to deliver a pacing pulse immediately upon receiving a trigger detect signal 124, either directly from receiver 120 or via control circuit 106. Alternatively, the pacing pulse may be delivered after a predetermined time delay.

When sensing circuit 114 is included in pacemaker 100, sensing circuit 114 may generate R-wave sensed event signals that are provided to pacemaker control circuit 106. Control circuit 106 may start a pacing timing interval upon receiving a trigger detect signal 124 from receiver 120. If an R-wave sense event signal is received by control circuit 106 from sensing circuit 114 prior to the pacing timing interval expiring, the scheduled pacing pulse is inhibited. No pacing pulse is delivered by pulse generator 112. If the pacing timing interval expires prior to receiving an R-wave sense event signal from sensing circuit 114, control circuit 106 enables pulse generator 112 to deliver the scheduled pacing pulse at the expiration of the pacing timing interval. An A-V or V-V interval set by ICD control circuit 80 to control the timing of timing control signal 95 and transmission of a trigger signal by emitting device 60 may take into account any inherent system delays and built-in timing delays so that a pacing pulse is ultimately delivered at a desired A-V or V-V interval.

The IMD systems shown in FIG. 1A, 3, and 5 are examples of systems that may utilize the techniques disclosed herein for automatically switching from atrial-synchronized to atrial-asynchronous ventricular pacing modes and back again. The examples shown and described herein are intended to be illustrative, not limiting. For example, another IMD system that may utilize the ventricular pacing mode switching techniques includes a subcutaneous sensing device that is configured to sense P-waves and emit trigger signals to an intracardiac pacemaker for controlling ventricular pacing but does not include cardioversion/defibrillation capabilities, e.g., as generally disclosed in U.S. Pat. Application No. 2016/0144190 (Cao, et al.), incorporated herein by reference in its entirety.

Figure 8:
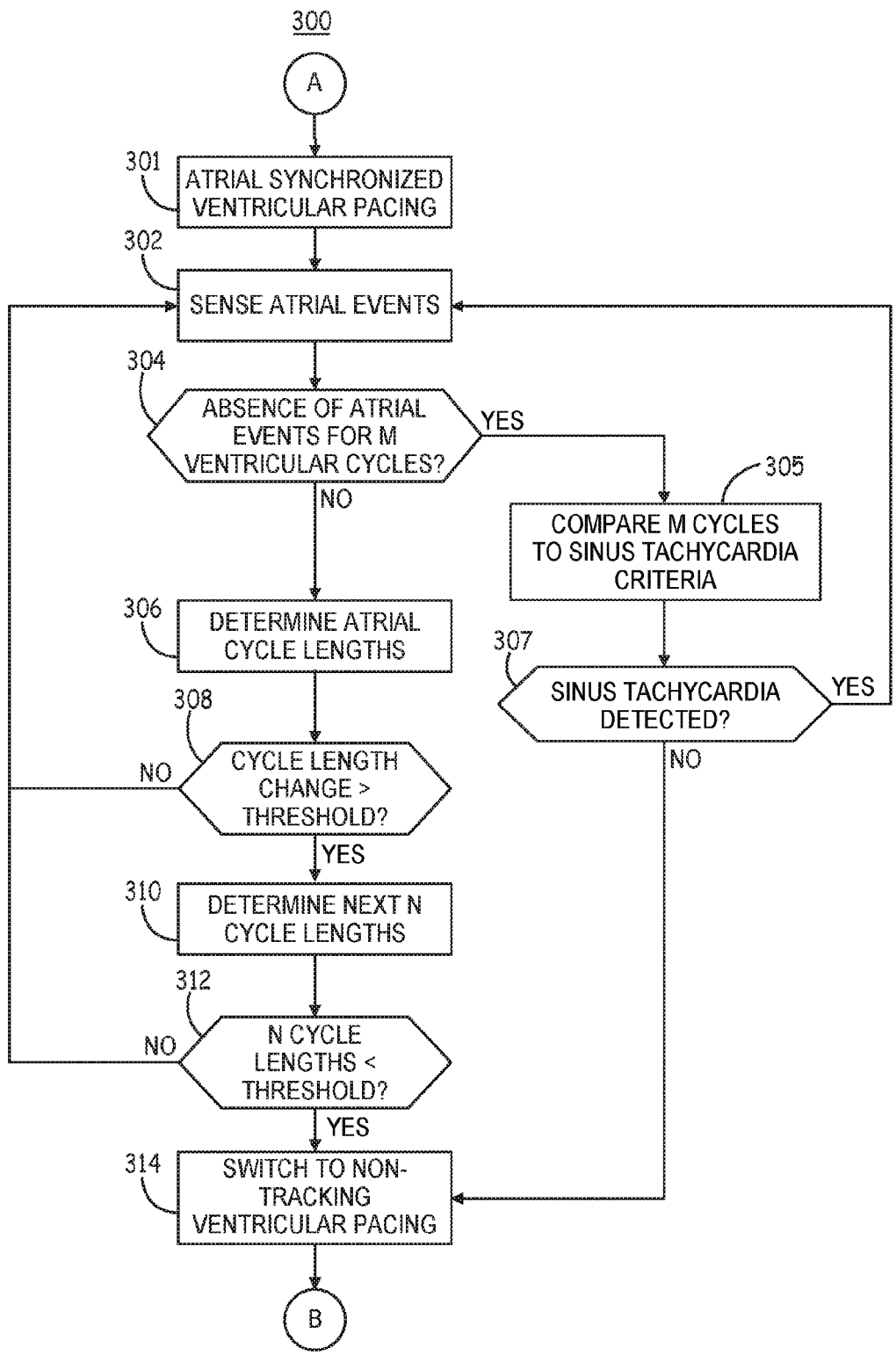
FIG. 8 and FIG. 9 are a flow chart of a method that may be performed by an IMD system for automatically switching between an atrial-synchronized ventricular pacing mode and an atrial-asynchronous ventricular pacing mode.
Figure 9:
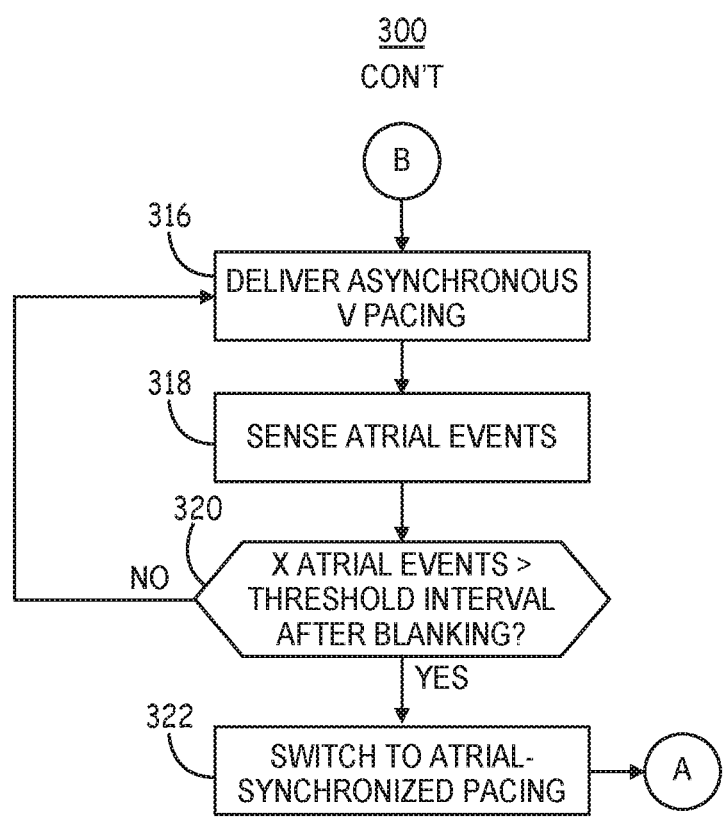

FIG. 8 and FIG. 9 show a flow chart 300 of a method that may be performed by an IMD system for automatically switching between an atrial-synchronized ventricular pacing mode and an atrial-asynchronous ventricular pacing mode. The method of FIG. 300 is performed by control circuitry of an IMD system, e.g., by control circuit 106 of pacemaker 100 (FIG. 1A) or by control circuit 80 of ICD 14 in system 10 (FIG. 3) or system 10' (FIG. 5). The IMD system may normally function in an atrial-synchronized ventricular pacing mode at block 301, e.g., a VDD(R) mode, in which both atrial events and ventricular events are sensed, and ventricular pacing pulses are triggered by atrial sensed events and delivered at a programmed A-V delay following the atrial sensed events and inhibited when an intrinsic ventricular event is sensed, e.g., when an R-wave is sensed prior to expiration of the A-V delay.

At block 302, the sensing circuit, e.g., sensing circuit 114 of pacemaker 100 or sensing circuit 86 of ICD 14, senses far-field atrial events, e.g., P-waves. Intra-cardiac, far-field P-wave sensing by pacemaker 100 or extra-cardiac, far-field P-wave sensing by ICD 14 from a cardiac electrical signal may be performed as described above or according to techniques disclosed in any of the incorporated references. Far-field P-wave sensing is further described below in conjunction with FIG. 10. Far-field atrial events may additionally or alternatively be sensed from a motion signal from accelerometer 118 positioned in the ventricle.

In pacemaker 100 and IMD system 10 or 10', P-waves are sensed from a far-field signal, e.g., a signal received by electrodes 162 and 164 positioned in the RV (FIG. 1A) or a signal received by extra-cardiovascular electrodes carried by lead 16 (FIG. 3) as opposed to being sensed from a near-field atrial signal received using electrodes positioned in or on an atrial chamber. As used herein, the term "far-field signal" is in reference to a cardiac electrical signal including P-waves or a cardiac motion signal including atrial motion signals that is acquired by electrodes or a motion sensor such as accelerometer 118, respectively, that are not positioned within or on an atrial chamber. When P-waves are sensed from a near-field signal, e.g., from electrodes positioned within the atrial chamber in a dual chamber pacemaker coupled to transvenous endocardial electrodes, confirmation of the atrial rate is relatively straight forward based on P-waves sensed from the near-field atrial signal. When the atrial rate determined from the near-field signal exceeds an upper tracking limit, the ventricular pacing mode may be switched from an atrial-tracking to a non-tracking pacing mode.

Since far-field atrial signals, e.g., P-waves, tend to be much smaller in amplitude than ventricular signals, e.g., R-waves, atrial sensing from a far-field signal can be challenging, particularly if the atrial P-waves become small during an atrial tachyarrhythmia such as atrial fibrillation or atrial flutter. Some P-waves may be missed such that the atrial rate may appear normal when determined based on PP intervals. In addition to having smaller amplitude, when the atrial rate is fast, atrial P-waves may occur during an atrial blanking period that is applied by sensing circuit 114 or sensing circuit 86 following an atrial sensed event. The resulting sensed atrial rate determined based on sensed P-waves outside an atrial blanking period may be slower than the actual atrial rate, e.g., half the actual rate if every other P-wave occurs during an atrial blanking period. As a result, the ventricular pacing mode may continue tracking atrial events during a fast atrial rate or atrial tachyarrhythmia, which may result in an irregular ventricular pacing rate or an unacceptably fast ventricular pacing rate.

Accordingly, rather than determining an atrial rate based on P-P intervals for controlling ventricular pacing mode switching, the control circuit (106 or 80) controlling the timing of ventricular pacing pulse delivery in pacemaker 100 or IMD system 10 or 10' may monitor atrial event signals for detecting an absence of atrial sensed events and/or for detecting a sudden change in atrial cycle length. At block 304, the control circuit determines if atrial events have not been sensed during a predetermined number of M ventricular cycles. For example, the control circuit may include a timer or counter to count the number of R-waves sensed with no intervening atrial events sensed as P-waves by the sensing circuit or sensed by the pacemaker control circuit 106 from a signal from accelerometer 118. If no atrial events are sensed for M ventricular cycles, e.g., for five to ten or other programmable number of ventricular cycles, the control circuit may switch immediately to a non-tracking (atrial asynchronous) ventricular pacing mode at block 314.

In some examples, however, if an absence of atrial events for M ventricular cycles is detected at block 304, the control circuit may analyze the M ventricular cycles for evidence of sinus tachycardia. At block 305, the M cycles are compared to sinus tachycardia criteria. For instance, a maximum ventricular cycle length threshold and or cycle length regularity criteria may be applied to the M cycles. In one example, if all M ventricular cycle lengths determined between consecutively sensed R-waves are less than a maximum ventricular cycle length, e.g., less than or equal to 500 ms, and are determined to be regular based on applied regularity criteria, then sinus tachycardia is detected at block 307. One example of regularity criteria that may be applied at block 305 may include determining the mean cycle length of the M ventricular cycle lengths and comparing the mean cycle length to each of the M cycle lengths. If the differences between the mean and each individual cycle length is less than a regularity threshold (for example less than 20 to 50 ms), the M ventricular cycle lengths are determined to be regular. This regularity is evidence of a sinus rhythm during which P-wave sensing may have been lost. Other metrics of regularity that may be determined and compared to a respective threshold may include cycle length range, standard deviation, modesum, etc.

If ventricular cycle length, regularity, and or other criteria for detecting sinus tachycardia are met by the M ventricular cycle lengths at block 305, sinus tachycardia is detected at block 307 and in this case, the control circuit remains in the atrial-synchronized ventricular pacing mode ("yes" branch of block 307) and waits until P-wave sensing returns. Since evidence of a sinus rhythm is present, with regularly sensed R-waves, switching to a non-tracking pacing mode is not performed. Pacing the ventricle at an unacceptably fast rate is not occurring since the P-waves are not being sensed and intrinsic R-waves are being sensed. In such cases, the control circuit waits until P-waves are sensed and delivers ventricular pacing in the atrial-synchronized pacing mode unless the sensed atrial cycle length meets mode-switching criteria as described below.

If sinus tachycardia is not detected at block 307 based on the comparison(s) made at block 305, the M ventricular cycle-lengths are irregular and/or long indicating a need to switch to an atrial-asynchronous (non-tracking) ventricular pacing mode. The absence of atrial events may indicate an atrial arrhythmia and to avoid an irregular ventricular rate, a pacing mode switch is warranted. The control circuit switches to the non-tracking pacing mode at block 314.

If atrial events are being sensed ("no" branch of block 304), the control circuit determines atrial cycle lengths at block 306. The atrial cycle lengths may be determined as P-P intervals between consecutive P-waves sensed by the sensing circuit 114 of pacemaker 100 or the sensing circuit 86 of ICD 14. In other examples, the atrial cycle lengths may be determined as time intervals between atrial events detected from a motion sensor, e.g., accelerometer 118, by pacemaker control circuit 100. The respective control circuit 106 or 80 compares one consecutive cycle length to the next consecutive cycle length at block 308. If the difference between two consecutive cycle lengths is greater than a cycle length change threshold, as determined at decision block 308, the control circuit 106 or 80 determines the next N atrial cycle lengths at block 310. The change in atrial cycle length is detected independent of the actual atrial rate. As such the sensed atrial rate may be any rate at the time the atrial cycle length change is detected, including rates that are faster or slower than an atrial tachyarrhythmia.

If the next N atrial cycle lengths are shorter than a cycle length threshold, as determined at decision block 312, the control circuit 106 or 80 switches from an atrial-tracking (synchronized) ventricular pacing mode to a non-tracking (atrial asynchronous) ventricular pacing mode at block 314. The cycle length threshold may be based on an atrial blanking period set by the control circuit or by the sensing circuit of pacemaker 100 or ICD 14. In one example, the atrial blanking period is at least 400 ms. In another example, the atrial blanking period is at least 500 ms. These examples are illustrative and longer or shorter atrial blanking periods may be used. The pacemaker control circuit 106 or ICD control circuit 80 may set the cycle length threshold to a predetermined time interval greater than the atrial blanking period. The predetermined time interval may be at least 60 ms in some examples.

If a change in cycle length greater than the change threshold is not detected ("no" branch of block 308) or N cycle lengths after a threshold cycle length change are not less than the cycle length threshold ("no" branch of block 312), the control circuit remains in the atrial synchronized pacing mode and continues to monitor atrial sensed events by returning to block 302. The control circuit 80 or 106 monitors atrial sensed events for detecting a pacing mode switch condition, e.g., absence of atrial sensed events for M ventricular cycles or a threshold cycle length change followed by N atrial cycle lengths less than the cycle length threshold.

If the pacing mode is switched to a non-tracking pacing mode at block 314, the process continues to FIG. 9 (flow chart 300 continued) as indicated by connector B. Asynchronous ventricular pacing is delivered at block 316 according to the non-tracking pacing mode. When the method of flow chart 300 is implemented in intracardiac pacemaker 100 implanted in a ventricular chamber, pacemaker control circuit 106 controls the pulse generator 112 to deliver asynchronous ventricular pacing at block 316, e.g., via the housing-based cathode electrode 164 and return anode electrode 162. When the method 300 is implemented in ICD 14 of an extra-cardiovascular ICD system 10, ICD control circuit 80 controls therapy delivery circuit 84 to deliver asynchronous ventricular pacing at block 316 via a selected extra-cardiovascular pacing electrode vector including at least one electrode carried by extra-cardiovascular lead 16, e.g., using pace/sense electrode 28 as a cathode electrode and defibrillation electrode 24 as a return anode though numerous other pacing electrode vectors may be selected. The asynchronous ventricular pacing is delivered by the respective pulse generator 112 or therapy delivery circuit 84 to a programmed pacing rate, e.g., 40 to 80 pulses per minute to provide bradycardia pacing support. In some examples, the ventricular pacing rate may be a rate-responsive rate set according to a sensor-indicated rate based on a patient activity metric determined from accelerometer 118. Upon switching to the non-tracking ventricular pacing mode, the pacing rate may be gradually adjusted to a targeted ventricular pacing rate to avoid a sudden ventricular rate change. A method for adjusting a ventricular pacing rate is generally disclosed in U.S. Pat. No. 5,893,882 (Peterson, et al.), incorporated herein by reference in its entirety.

When the method of flow chart 300 is implemented in a triggered pacing system, e.g., system 10' of FIG. 5, the ICD control circuit 80 passes a timing control signal 95 to emitting device 60 at the desired ventricular pacing rate. In this way, emitting device 60 transmits a trigger signal to pacemaker 100 at the desired ventricular pacing rate to control intracardiac pacemaker 100 to deliver ventricular pacing at the atrial asynchronous ventricular pacing rate.

During ventricular pacing, atrial events are still sensed at block 318 for monitoring a return of atrial events that meet criteria for switching back to atrial synchronized ventricular pacing. As such, the non-tracking ventricular pacing mode may be a VDI(R) pacing mode in which both atrial and ventricular events are sensed and ventricular pacing pulses are inhibited when an intrinsic R-wave is sensed during a V-V pacing escape interval. Sensed atrial events may be analyzed by pacemaker control circuit 106 or ICD control circuit 80 by determining atrial event time intervals. Atrial time intervals may be determined and analyzed on a beat-by-beat basis or periodically during the asynchronous ventricular pacing mode, e.g., after every 8 to 12 ventricular pacing pulses or another predetermined number of pacing pulses.

Atrial time intervals may be determined at block 320 relative to an atrial blanking period applied to pacemaker sensing circuit 114 or ICD sensing circuit 86 after an atrial sensed event. A relatively high sensitivity is used for sensing low amplitude P-waves from a far-field cardiac electrical signal. In order to avoid noise, ventricular events or other artifact being falsely sensed as P-waves, a relatively long post-atrial sensing blanking period may be applied. The atrial blanking period may be up to 500 ms or even up to 650 ms. During blanking, atrial events are not sensed. As such, atrial events occurring during the blanking period when the atrial rate is high may go un-sensed such that atrial rate alone may not be reliable for controlling ventricular pacing mode switching. In some examples, therefore, rather than determining P-P intervals (or atrial event intervals from a motion sensor), atrial time intervals are determined as the time interval from the expiration of the atrial blanking period to the sensed atrial event.

At block 320, pacemaker control circuit 106 or ICD control circuit 80 determines time intervals from the end of the atrial blanking period to the next sensed atrial event for X atrial sensed events. The X atrial sensed events may be consecutive atrial events. If a predetermined number of atrial events are sensed more than a threshold time interval after the atrial blanking period expires, "yes" branch of block 320, the pacemaker control circuit 106 or ICD control circuit 80 switches back to the atrial synchronized ventricular pacing mode at block 322. The process returns to block 301 as indicated by connector A.

The predetermined number of atrial events sensed more than the threshold time interval after blanking period expiration may be X consecutive atrial events or X out of Y consecutive atrial events. For example, at least five to ten consecutive atrial events may be required to be sensed more than 60 ms after the expiration of the atrial blanking period. In another example, at least five non-consecutive atrial events out of eight consecutive atrial events may be required to be at least 60 ms after the expiration of the atrial blanking period. When a threshold number of atrial events are regularly sensed after a threshold interval after the atrial blanking period expires, the atrial rhythm is expected to have returned to a normal rhythm and atrial tracking of the ventricular pacing pulses may be resumed. The process returns to block 301 (FIG. 8) as indicated by connector A to deliver ventricular pacing pulses in the atrial synchronized ventricular pacing mode.

Figure 10:
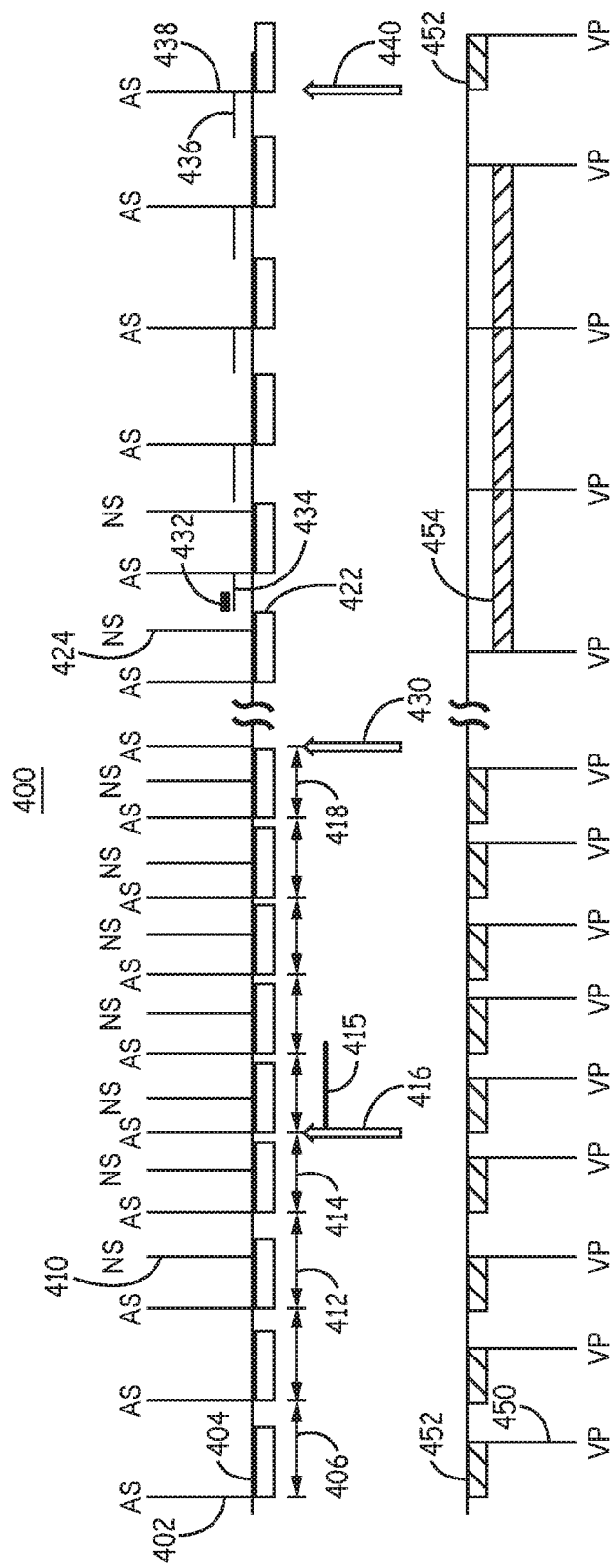
FIG. 10 is a timing diagram of atrial events, e.g., far-field P-waves, sensed by an IMD sensing circuit, used to control ventricular pacing mode switching.

FIG. 10 is a timing diagram 400 of atrial events, e.g., P-waves, sensed by pacemaker sensing circuit 114 or ICD sensing circuit 86. Atrial events sensed by pacemaker sensing circuit 114 or ICD sensing circuit 86 are denoted by "AS." Each AS event 402 is followed by an atrial blanking period 404, during which no atrial event sensing occurs. Atrial events that occur during a blanking period 404, such as event 410, are labeled "non-sensed" or "NS." Initially the pacemaker 100, ICD 14, or triggered pacing system 10' is operating in an atrial-synchronized ventricular pacing mode during which ventricular pacing pulses (VP) 450 are delivered upon expiration of an A-V interval 452. Each A-V interval 452 is started in response to an AS event.

When the atrial rate increases, for example at the onset of an atrial tachyarrhythmia, some atrial events occur during the atrial blanking period 404 and are non-sensed events (NS) 410. When the atrial events are sensed from a far-field signal, a high sensitivity may be used with a relatively long atrial blanking period 404 to prevent atrial oversensing. As a result, determination of the atrial rate based on P-P intervals, e.g., intervals 406, 412 and 414, between two consecutive AS events, may not be reliable for controlling pacing mode switching because some atrial events may occur during the relatively long blanking period 404.

As described in conjunction with FIG. 8, pacemaker control circuit 106 or ICD control circuit 86 may determine atrial event cycle lengths, e.g., as P-P intervals between consecutive AS events. At time 416, control circuit 106 or 80 detects a cycle length change between two consecutive atrial cycle lengths 412 and 414 that is greater than a cycle length change threshold. Atrial cycle length 414 is shorter than the immediately preceding atrial cycle length 412 by more than the cycle length change threshold. In other examples, an atrial cycle length change between non-consecutive atrial cycle lengths may be compared to a change threshold. In response to detecting the change in cycle length that is greater than the change threshold (the change being a decrease in cycle length), the control circuit 106 or 80 determines if the next N atrial cycle lengths are all less than a cycle length threshold 415.

In the example of FIG. 10, the atrial cycle length 418 is the fifth consecutive cycle length less than the cycle length threshold 415 after a change in consecutive cycle lengths that is greater than the change threshold detected at time 416. In this example, this combination of a cycle length change exceeding the change threshold followed by 5 cycle lengths less than the cycle length threshold 415 meets pacing mode switching criteria. The pacemaker control circuit 106 or ICD control circuit 80 switches the pacing mode of operation from the atrial-synchronized pacing mode to the non-tracking, atrial-asynchronous pacing mode at time 430.

Thereafter, ventricular pacing pulses are delivered at a non-tracking ventricular pacing rate controlled by setting a V-V interval 454. When the V-V interval expires, a pacing pulse (VP) is delivered. If an intrinsic R-wave is sensed during the V-V interval 454, the pacing pulse is inhibited. The ventricular pacing pulses are asynchronous with the sense atrial events (AS).

During this non-tracking, atrial-asynchronous pacing mode, the pacemaker control circuit 106 or the ICD control circuit 80 monitors atrial sensed events to determine when criteria for switching back to the atrial-synchronized pacing mode are satisfied. Since some atrial events, such as NS event 424 may occur during the relatively long atrial blanking period applied to the far-field atrial signal, determination of the atrial rate based on AS events may not be reliable for detecting when the atrial rate falls below an upper tracking rate or is slower than an atrial tachyarrhythmia rate. Instead, pacemaker control circuit 106 or ICD control circuit 80 determines atrial time interval 434 between the time of expiration 422 of an atrial blanking period and the next AS event. During the fast atrial rate prior to mode switching at time 430, the time intervals from the expiration of each blanking period to the next respective AS event are observed to be very short. As the atrial rate slows, the atrial time interval 434 from the blanking period expiration 422 to the immediately subsequent AS event increases and will eventually remain greater than a predetermined interval threshold 432 during a normal, stable atrial rate.

Pacemaker control circuit 106 or ICD control circuit 80 may determine and monitor this atrial time interval following each atrial blanking period 404 until a predetermined number of AS events occur at least a threshold interval 432 after the blanking period expiration 422. For example, AS event 438 occurs at an atrial time interval 436 that is the fifth consecutive atrial time interval (starting with atrial time interval 432) that is greater than the interval threshold 432. In response to detecting five atrial time intervals greater than the interval threshold 432, the control circuit 106 or 80 switches back to atrial-synchronized ventricular pacing at time 440. The next pacing pulse is scheduled and delivered at an A-V interval 452 following AS event 438.

It is recognized that in some cases switching between atrial-synchronized and atrial-asynchronous ventricular pacing may not occur on a single pacing cycle; one additional pacing cycle may occur according to the current pacing mode before switching to the new pacing mode after detecting that mode switching criteria are met. Furthermore, the pacing rate may be adjusted gradually toward a target V-V interval or target A-V interval to avoid abrupt changes in pacing rate.

As can be seen in FIG. 10, rather than relying on determining an atrial rate or detecting an atrial tachyarrhythmia for controlling pacing mode switching, initially a threshold change in atrial cycle length is required before switching from an atrial-synchronized pacing mode to a non-tracking mode. For example, if atrial events are initially being sensed at approximately 800 to 1000 ms cycle lengths, a sudden change in cycle length greater than 100 ms, e.g., a drop to sensed atrial cycle lengths of 500 to 700 ms, may be evidence of a fast atrial rate that is above a desired tracking rate, even though the atrial cycle lengths determined between sensed atrial events may still be greater than an atrial tachyarrhythmia cycle length or upper tracking rate, e.g., greater than 500 ms. This may occur when a long atrial blanking period, which may be adaptable to the current cycle length such as an atrial blanking period of 40 to 50 percent of the current cycle length, is applied to prevent oversensing of T-waves or other ventricular activity by the atrial sensing channel. Atrial events that occur at atrial cycle lengths shorter than the blanking period will not be sensed during the long blanking period. The sudden change in cycle length that is greater than the change threshold may indicate that a rate change has occurred and some atrial events may be under-sensed during the atrial blanking period. The sensed atrial cycle lengths following the threshold change in atrial cycle length may remain greater than an upper atrial tracking rate or an atrial tachyarrhythmia rate that might normally be used for controlling mode switching in a dual chamber pacemaker when atrial events are sensed from a near field signal.

As the atrial rate slows again or returns to a sinus rhythm, some atrial events may still occur during the atrial blanking period, e.g., NS event 424, but as the rate slows even more, the atrial events will occur at intervals longer than the blanking period and will eventually occur at time intervals after the expiration of the blanking period that are consistently greater than an interval threshold 432. Even if some atrial events occur during the atrial blanking period, switching to the atrial-synchronized pacing mode results in ventricular pacing at a pacing rate interval that tracks only the atrial events sensed outside of the atrial blanking period by a predetermined time interval, e.g., 60 ms outside a 500 ms atrial blanking period in the example above, which may be considered a safe ventricular pacing rate interval. At this point, switching back to an atrial-synchronized pacing mode may be performed without having to rely on determining actual atrial cycle lengths or an actual atrial rate.

Thus, a method and apparatus for controlling ventricular pacing mode in an IMD system have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A system comprising at least one implantable medical device, the system comprising:
   a sensing circuit configured to receive a cardiac signal comprising far-field atrial events;
   a therapy delivery circuit configured to deliver ventricular pacing pulses via electrodes coupled to the therapy delivery circuit;
   at least one memory configured to store instructions;
   at least one control circuit configured, according to the instructions, to:
      control the therapy delivery circuit to deliver the ventricular pacing pulses in an atrial-synchronized pacing mode;
      during the atrial synchronized pacing mode, determine atrial cycle lengths between far-field atrial events sensed from the cardiac signal;
      detect a cycle length change between two atrial cycle lengths that is greater than a cycle length change threshold by determining a difference between the two atrial cycle lengths and comparing the difference to the cycle length change threshold;
      determine if first pacing mode switching criteria are satisfied subsequent to detecting the cycle length change; and
      in response to the first pacing mode switching criteria being satisfied, switch from the atrial-synchronized ventricular pacing mode to an atrial-asynchronous pacing mode for controlling the therapy delivery circuit in delivering the ventricular pacing pulses; and
   at least one power source configured to power the a sensing circuit, therapy delivery circuit, the memory, and the control circuit.

2. The system of claim 1, wherein the control circuit is further configured to:
   sense ventricular events from the cardiac electrical signal;
   determine ventricular cycle lengths between consecutive pairs of the sensed ventricular events;
   detect an absence of far-field atrial events in the cardiac signal over a predetermined number of the ventricular cycle lengths;
   in response to detecting the absence of the far-field atrial events, compare the predetermined number of ventricular cycle lengths to sinus tachycardia detection criteria; and
   remain in the atrial-synchronized ventricular pacing mode in response to the predetermined number of ventricular cycle lengths meeting the sinus tachycardia detection criteria.

3. The system of claim 1, wherein, to determine if the first pacing mode switching criteria are satisfied, the control circuit is configured to:
   determining determine atrial cycle lengths between far-field atrial events of the cardiac signal after detecting the cycle length change;
   compare the atrial cycle lengths to a cycle length threshold; and
   determine the pacing mode switching criteria are satisfied when a predetermined number of the atrial cycle lengths after the cycle length change are less than the cycle length threshold.

4. The system of claim 1, wherein:
   the sensing circuit is configured to:
      sense at least a portion of the far-field atrial events from the cardiac signal; and
      set an atrial blanking period in response to each sensed far-field atrial event such that far-field atrial events that occur during the atrial blanking period are not sensed; and
   wherein the control circuit determines the atrial cycle lengths between consecutive ones of the sensed far-field atrial events.

5. The system of claim 4, wherein the control circuit is configured to set the cycle length threshold to a predetermined time interval greater the atrial blanking period.

6. The system of claim 5, wherein the atrial blanking period is at least 400 ms and the predetermined time interval is at least 60 ms.

7. The system of claim 4, wherein the control circuit is further configured to:
   during the atrial-asynchronous ventricular pacing mode, determine an atrial time interval between an expiration of the atrial blanking period and a next sensed far-field atrial event;
   compare the atrial time interval to a threshold interval;
   determine if second pacing mode switching criteria are satisfied in response to the atrial time interval being greater than the threshold interval; and
   switch from the atrial-asynchronous pacing mode back to the atrial-synchronized pacing mode in response to the second pacing mode switching criteria being satisfied.

8. The system of claim 7, wherein, to determine if the second pacing mode switching criteria are satisfied, the control circuit is configured to:
   determine a plurality of atrial time intervals between each one of an expiration of the respective atrial blanking period and a subsequent sensed far-field atrial event; and
   determine that the second pacing mode switching criteria are satisfied when a threshold number of the atrial time intervals are greater than the threshold interval.

9. The system of claim 1, wherein the cycle length change threshold is a decrease of at least 100 ms from a first atrial cycle length to a next atrial cycle length consecutively following the first atrial cycle length.

10. The system of claim 1, further comprising a motion sensor producing the cardiac signal.

11. The system of claim 1, wherein the at least one implantable medical device comprises an intracardiac pacemaker, the intracardiac pacemaker comprising a housing enclosing the sensing circuit, the therapy delivery circuit and the control circuit.

12. The system of claim 1, wherein the at least one implantable medical device comprises an extra-cardiovascular implantable cardioverter defibrillator comprising a housing enclosing the sensing circuit, the therapy delivery circuit and the control circuit,
   the system further comprising an extra-cardiovascular lead comprising a plurality of extra-cardiovascular electrodes that are coupled to the sensing circuit and the therapy delivery circuit when the extra-cardiovascular lead is coupled to the implantable cardioverter defibrillator,
   the sensing circuit configured to receive the cardiac signal via at least one extra-cardiovascular electrode carried by the lead, and
   the therapy delivery circuit configured to deliver the ventricular pacing pulses via at least one extra-cardiovascular electrode carried by the lead.

13. The system of claim 1, wherein the at least one implantable medical device comprises:
   an intra-cardiac pacemaker comprising:
      a housing enclosing the therapy delivery circuit; and
      a trigger signal receiver; and
      wherein at least one of the electrodes coupled to the therapy delivery circuit for delivering the ventricular pacing pulses is housing-based;
   an extra-cardiovascular implantable cardioverter defibrillator comprising a housing enclosing the sensing circuit and the at least one control circuit; and
   an emitting device comprising a transducer configured to produce a trigger signal transmitted wirelessly to the trigger signal receiver of the pacemaker;
   the system further comprising an extra-cardiovascular lead comprising a plurality of extra-cardiovascular electrodes that are coupled to the sensing circuit when the extra-cardiovascular lead is coupled to the implantable cardioverter defibrillator, the sensing circuit configured to receive the cardiac signal comprising far-field atrial events via at least one extra-cardiovascular electrode carried by the lead;
   the at least one control circuit further configured to control the therapy delivery circuit to deliver the ventricular pacing pulses by transmitting a timing control signal to the emitting device,
   the emitting device configured to transmit the trigger signal to the trigger signal receiver in response to receiving the timing control signal; and
   the therapy delivery circuit configured to deliver at least one ventricular pacing pulse in response to the trigger signal receiver receiving the trigger signal.

14. A method for controlling a ventricular pacing mode by a system comprising at least one implantable medical device, the system comprising: a sensing circuit; a therapy delivery circuit; at least one memory configured to store instructions; at least one control circuit configured according to the instructions; and at least one power source configured to power the sensing circuit, therapy delivery circuit, the memory, and the control circuit, the method comprising:
   receiving, by the sensing circuit, a cardiac signal comprising far-field atrial events;
   controlling, by the at least one control circuit, the therapy delivery circuit to deliver ventricular pacing pulses in an atrial-synchronized pacing mode via electrodes coupled to the therapy delivery circuit;
   during the atrial synchronized pacing mode, determining by the at least one control circuit, atrial cycle lengths between far-field atrial events sensed from the cardiac signal;
   detecting, by the at least one control circuit, a cycle length change between two atrial cycle lengths that is greater than a cycle length change threshold by determining a difference between the two atrial cycle lengths and comparing the difference to the cycle length change threshold;
   determining, by the at least one control circuit, if first pacing mode switching criteria are satisfied subsequent to detecting the cycle length change; and
   in response to the first pacing mode switching criteria being satisfied, switching, by the at least one control circuit, from the atrial-synchronized ventricular pacing mode to an atrial-asynchronous pacing mode for controlling the therapy delivery circuit by the control circuit in delivering the ventricular pacing pulses.

15. The method of claim 14, further comprising:
   sensing ventricular events from the cardiac electrical signal;
   determining ventricular cycle lengths between consecutive pairs of the sensed ventricular events;
   detecting an absence of far-field atrial events in the cardiac signal over a predetermined number of the ventricular cycle lengths;
   in response to detecting the absence of the far-field atrial events, comparing the predetermined number of ventricular cycle lengths to sinus tachycardia detection criteria; and
   remaining in the atrial-synchronized ventricular pacing mode in response to the predetermined number of ventricular cycle lengths meeting the sinus tachycardia detection criteria.

16. The method of claim 14, wherein determining if the first pacing mode switching criteria are satisfied comprises:
   determining atrial cycle lengths between far-field atrial events of the cardiac signal after detecting the cycle length change;
   comparing the atrial cycle lengths to a cycle length threshold; and
   determining the pacing mode switching criteria are satisfied when a predetermined number of the atrial cycle lengths after the cycle length change are less than the cycle length threshold.

17. The method of claim 16, further comprising:
during the atrial-asynchronous ventricular pacing mode, determining an atrial time interval between an expiration of the atrial blanking period and a next sensed far-field atrial event;
comparing the atrial time interval to a threshold interval;
determining if second pacing mode switching criteria are satisfied in response to the atrial time interval being greater than the threshold interval; and
switching from the atrial-asynchronous pacing mode back to the atrial-synchronized pacing mode in response to the second pacing mode switching criteria being satisfied.

18. The method of claim 17, wherein determining if the second pacing mode switching criteria are satisfied comprises:
determining a plurality of atrial time intervals between each one of an expiration of the respective atrial blanking period and a subsequent sensed far-field atrial event; and
determining that the second pacing mode switching criteria are satisfied when a threshold number of the atrial time intervals are greater than the threshold interval.

19. The method of claim 14, further comprising:
sensing at least a portion of the far-field atrial events from the cardiac signal;
setting an atrial blanking period in response to each sensed far-field atrial event such that far-field atrial events that occur during the atrial blanking period are not sensed; and
determining the atrial cycle lengths between consecutive ones of the sensed far-field atrial events.

20. The method of claim 19, further comprising setting the cycle length threshold to a predetermined time interval greater the atrial blanking period.

21. The method of claim 20, further comprising setting the atrial blanking period to at least 400 ms and setting the predetermined time interval to at least 60 ms.

22. The method of claim 14, wherein detecting the cycle length change comprises detecting a cycle length change that is a decrease of at least 100 ms from a first atrial cycle length to a next atrial cycle length consecutively following the first atrial cycle length.

23. The method of claim 14, further comprising determining the atrial cycle lengths between far-field atrial events sensed from a motion sensor signal.

24. The method of claim 14, wherein the at least one implantable medical device comprises an intracardiac pacemaker, the intracardiac pacemaker comprising a housing enclosing the sensing circuit, the therapy delivery circuit and the control circuit,
the method comprising delivering the ventricular pacing pulses via at least one housing-based electrode coupled to the therapy delivery circuit of the intracardiac pacemaker.

25. The method of claim 14, wherein the at least one implantable medical device comprises an extra-cardiovascular implantable cardioverter defibrillator comprising a housing enclosing the sensing circuit, the therapy delivery circuit and the control circuit,
the system further comprising an extra-cardiovascular lead comprising a plurality of extra-cardiovascular electrodes that are coupled to the sensing circuit and the therapy delivery circuit when the extra-cardiovascular lead is coupled to the implantable cardioverter defibrillator,
the method further comprising:
receiving the cardiac signal by the sensing circuit via at least one extra-cardiovascular electrode carried by an extra-cardiovascular lead coupled to the implantable cardioverter defibrillator, and
delivering the ventricular pacing pulses via at least one extra-cardiovascular electrode carried by the lead.

26. The method of claim 14, wherein the system comprises:
an intra-cardiac pacemaker comprising:
a housing enclosing the therapy delivery circuit; and
a trigger signal receiver; and
wherein at least one of the electrodes coupled to the therapy delivery circuit for delivering the ventricular pacing pulses is housing-based;
an extra-cardiovascular implantable cardioverter defibrillator comprising a housing enclosing the sensing circuit and the at least one control circuit; and
an emitting device comprising a transducer configured to produce a trigger signal transmitted wirelessly to the trigger signal receiver of the pacemaker;
the system further comprising an extra-cardiovascular lead comprising a plurality of extra-cardiovascular electrodes that are coupled to the sensing circuit when the extra-cardiovascular lead is coupled to the implantable cardioverter defibrillator, the sensing circuit configured to receive the cardiac signal comprising far-field atrial events via at least one extra-cardiovascular electrode carried by the lead;
the method comprising:
controlling the therapy delivery circuit to deliver the ventricular pacing pulses by transmitting timing control signals from the at least one control circuit to an emitting device,
transmitting a trigger signal from the emitting device to the intracardiac pacemaker in response to each timing control signal; and
delivering the ventricular pacing pulses by the therapy delivery circuit included in the intracardiac pacemaker in response to receiving the trigger signals.

27. A non-transitory, computer-readable storage medium comprising a set of instructions executable by at least one control circuit of an implantable medical device system, wherein the implantable medical device system comprises: a sensing circuit; a therapy delivery circuit; at least one control circuit; and at least one power source configured to power the sensing circuit, therapy delivery circuit, and the at least one control circuit, wherein when executed by the at least one control circuit, the instructions cause the system to:
receive by the sensing circuit a cardiac signal comprising far-field atrial events;
control the therapy delivery circuit to deliver ventricular pacing pulses in an atrial-synchronized pacing mode via electrodes coupled to the therapy delivery circuit;
during the atrial synchronized pacing mode, determine atrial cycle lengths between far-field atrial events sensed from the cardiac signal;
detect a cycle length change between two atrial cycle lengths that is greater than a cycle length change threshold by determining a difference between the two atrial cycle lengths and comparing the difference to the cycle length change threshold;
determine if pacing mode switching criteria are satisfied subsequent to detecting the cycle length change; and
in response to the pacing mode switching criteria being satisfied, switch from the atrial-synchronized ventricular pacing mode to an atrial-asynchronous pacing mode for controlling the therapy delivery circuit in delivering the ventricular pacing pulses.

* * * * *